United States Patent
Oda

(12) 
(10) Patent No.: US 11,432,784 B2
(45) Date of Patent: Sep. 6, 2022

(54) RADIOGRAPHIC IMAGE DETECTION DEVICE, METHOD FOR OPERATING RADIOGRAPHIC IMAGE DETECTION DEVICE, AND PROGRAM FOR OPERATING RADIOGRAPHIC IMAGE DETECTION DEVICE

(71) Applicant: FUJIFILM CORPORATION, Tokyo (JP)

(72) Inventor: Yasufumi Oda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 97 days.

(21) Appl. No.: 17/163,596

(22) Filed: Feb. 1, 2021

(65) Prior Publication Data

US 2021/0251586 A1    Aug. 19, 2021

(30) Foreign Application Priority Data

Feb. 17, 2020    (JP) .............................. JP2020-024651

(51) Int. Cl.
*A61B 6/00*    (2006.01)

(52) U.S. Cl.
CPC .................. *A61B 6/42* (2013.01); *A61B 6/40* (2013.01); *A61B 6/5205* (2013.01)

(58) Field of Classification Search
CPC ..... A61B 6/4233; A61B 6/4266; A61B 6/463; A61B 6/5205; A61B 6/4283; G06T 2207/10116; G06T 2207/00; G06T 2207/20172; G06T 2207/20221; G01T 1/247; H01L 27/14676

See application file for complete search history.

(56) References Cited

FOREIGN PATENT DOCUMENTS

JP    2007330302 A  * 12/2007
JP    2014-168602 A    9/2014

* cited by examiner

*Primary Examiner* — Don K Wong
(74) *Attorney, Agent, or Firm* — Solaris Intellectual Property Group, PLLC

(57) ABSTRACT

At least two first offset images having different accumulation times are acquired in a state in which radiation is not emitted. A pixel signal is read in an accumulation time shorter than that of a plurality of first offset images or using binning reading in a state in which the radiation is not emitted to acquire a second offset image. A reference image is acquired by reading the pixel signal using the same reading method as that used for the second offset image and in a state in which gates of the pixels are turned off. A difference between the two first offset images having different accumulation times is calculated to acquire a first dark current distribution image. A difference between the second offset image and the reference image is calculated to acquire a second dark current distribution image. It is determined whether or not reacquisition is needed on the basis of a correction error of a corrected image obtained by correcting the first dark current distribution image on the basis of the second dark current distribution image.

8 Claims, 21 Drawing Sheets

RADIOGRAPHIC IMAGE DETECTION DEVICE, METHOD FOR OPERATING RADIOGRAPHIC IMAGE DETECTION DEVICE, AND PROGRAM FOR OPERATING RADIOGRAPHIC IMAGE DETECTION DEVICE

CROSS-REFERENCE TO RELATED APPLICATIONS

The present application claims priority under 35 U.S.C. § 119 to Japanese Patent Application No., 2020-024651 filed on Feb. 17, 2020. The above application is hereby expressly incorporated by reference, in its entirety, into the present application.

BACKGROUND

1. Technical Field

The technology of the present disclosure relates to a radiographic image detection device, a method for operating the radiographic image detection device, and a program for operating the radiographic image detection device.

2. Description of the Related Art

In the medical field, an X-ray imaging system that uses, for example, X-rays as radiation is known. The X-ray imaging system includes an X-ray generation apparatus that generates X-rays and an X-ray imaging apparatus that detects the X-rays, which have been generated by the X-ray generation apparatus and transmitted through a patient as a subject, to capture a radiographic image. The X-ray imaging apparatus includes an X-ray image detection device that detects an X-ray image based on the X-rays transmitted through the subject and a console that performs, for example, the control of the driving of the X-ray image detection device and the storage and display of the X-ray image.

The X-ray image detection devices include a direct conversion type that directly converts X-rays into charge and an indirect conversion type that converts X-rays into visible light and then converts the visible light into charge. In any of the types, the X-ray image detection device has a pixel region in which a plurality of pixels detecting X-rays are arranged and a reading unit that reads a pixel signal from the pixel region, and generates an X-ray image on the basis of the pixel signal read by the reading unit.

The X-ray image detected by the X-ray image detection device includes, for example, dark current noise generated in each pixel and fixed pattern noise generated by a charge amplifier and the like included in the reading unit. Offset data is acquired in advance before X-ray imaging in order to remove the noise components from the X-ray image. The offset data is acquired by reading the pixel signal from the pixel region in a state in which no X-rays are emitted. The offset data is data including only noise components. After the offset data is acquired, offset correction for subtracting the offset data from the X-ray image obtained by the X-ray imaging is performed to obtain an X-ray image from which noise has been removed.

Of the dark current noise and the fixed pattern noise included in the offset data, the dark current noise changes depending on the temperature. Therefore, a time interval from the acquisition of the offset data to the X-ray imaging is long. In a case in which the temperature changes during the time, a dark current noise component changes, which results in a reduction in the accuracy of offset correction. For this reason, it is ideal to acquire the offset data immediately before the X-ray imaging is performed, in order to improve the accuracy of offset correction.

However, in a case in which the offset data is acquired immediately before the X-ray imaging, a time lag occurs between the instruction to perform the X-ray imaging and the actual X-ray imaging. As a result, there is a possibility that the X-ray image intended by the radiographer will not be obtained. Therefore, a technique has been proposed in which an X-ray image detection device is driven in a time shorter than the irradiation time of X-ray imaging or in a binning mode to perform an offset data acquisition operation immediately before the X-ray imaging (see JP2014-168602A).

SUMMARY

JP2014-168602A discloses a technique which acquires offset data (hereinafter, referred to as a first offset image) during calibration, such as during maintenance, in addition to the acquisition of offset data (hereinafter, referred to as an immediately preceding offset image) immediately before the X-ray imaging. The first offset image is obtained by reading a pixel signal from a pixel region using the same reading method as in the X-ray imaging in a state in which no X-rays are emitted.

Further, it is considered that a pixel signal is read by the same reading method as that used for the immediately preceding offset image to acquire offset data (hereinafter, referred to as a second offset image) during calibration.

Offset correction is performed on the X-ray image generated by the X-ray imaging using the first offset image, the second offset image, and the immediately preceding offset image acquired in advance. For example, the X-ray image is corrected by subtracting a difference image between the second offset image and the immediately preceding offset image in addition to the subtraction of the first offset image. The difference image corresponds to the amount of variation in dark current noise from the calibration to the X-ray imaging. Therefore, in the correction process, the amount of variation in dark current noise is corrected on the basis of the difference image, in addition to the offset correction on the X-ray image using the first offset image.

In the correction process, in a case in which there is a difference between the dark current distributions in the first offset image and the second offset image acquired during the calibration, there is a concern that the accuracy of correcting the dark current noise on the basis of the difference image will be reduced.

In addition, in the X-ray imaging, charge is accumulated in the accumulation time corresponding to the X-ray irradiation time. Therefore, it is preferable to acquire a plurality of first offset images having different accumulation times for X-ray imaging operations having different irradiation times during calibration. However, in a case in which a plurality of first offset images are acquired during calibration as such, the calibration time increases (for example, by several tens of seconds), and there is a possibility that a temperature change will occur during the calibration.

In a case in which the temperature changes during the calibration as such, the dark current distribution in the plurality of first offset images acquired during the calibration changes. For example, in a case in which the calibration is performed immediately after the X-ray image detection device is started up, a large temperature change occurs due to the influence of the heat generated by an electric substrate or the like in the X-ray imaging apparatus. Therefore, there is a high possibility that the dark current distribution will change during the calibration.

Therefore, among the plurality of acquired first offset images, one first offset image is selected and used for the offset correction of the X-ray image. However, there is a concern that the dark current distribution will be largely different from that of the second offset image, depending on the selected first offset image, and the accuracy of correcting the dark current noise will be reduced.

Therefore, in a case in which there is a difference between the dark current distributions of the first offset image and the second offset image, it is not desirable to correct the X-ray image using the offset images. Therefore, it is desirable to determine the validity of using the acquired first offset image and second offset image for the correction of the X-ray image and to reacquire the first offset image and the second offset image in a case in which the use is not valid.

An object of the technology of the present disclosure is to provide a radiographic image detection device that can determine whether or not an offset image acquired during calibration needs to be reacquired, a method for operating the radiographic image detection device, and a program for operating the radiographic image detection device.

In order to achieve the above object, according to an aspect of the present disclosure, there is provided a radiographic image detection device comprising: a pixel region in which a plurality of pixels detecting radiation are arranged; a reading unit that reads a pixel signal from the pixel region; and at least one processor. The processor performs: a first offset image acquisition process of reading the pixel signal from the pixel region in a state in which the radiation is not emitted to acquire at least two first offset images having different accumulation times; a second offset image acquisition process of reading the pixel signal from the pixel region in an accumulation time shorter than that of the plurality of first offset images or using binning reading in a state in which the radiation is not emitted to acquire a second offset image; a reference image acquisition process of reading the pixel signal from the pixel region using the same reading method as that used for the second offset image and in a state in which gates of the pixels are turned off to acquire a reference image; a first dark current distribution image acquisition process of calculating a difference between the two first offset images having different accumulation times to acquire a first dark current distribution image; a second dark current distribution image acquisition process of calculating a difference between the second offset image and the reference image to acquire a second dark current distribution image; and a determination process of determining whether or not the first offset image and the second offset image need to be reacquired on the basis of a correction error of a corrected image obtained by correcting the first dark current distribution image on the basis of the second dark current distribution image.

Preferably, in a case in which the correction error is equal to or greater than a threshold value, the processor determines that the first offset image and the second offset image need to be reacquired.

Preferably, the processor acquires the second offset image using the second offset image acquisition process immediately before the first offset image is acquired by the first offset image acquisition process.

Preferably, in a case in which the pixel signal is read by the binning reading to acquire the second offset image and the reference image, the processor performs the correction after performing an enlargement and reduction process of matching image sizes of the first dark current distribution image and the second dark current distribution image in the determination process.

Preferably, the processor performs: a radiographic image generation process of reading the pixel signal from the pixel region in a state in which the radiation is emitted to generate a radiographic image; an immediately preceding offset image acquisition process of acquiring an immediately preceding offset image using the same reading method as that used for the second offset image in a state in which the radiation is not emitted immediately before radiography including the radiographic image generation process; and a correction process of correcting the radiographic image on the basis of the first offset image, the second offset image, and the immediately preceding offset image.

Preferably, the correction process includes: a selection process of selecting the first offset image corresponding to imaging conditions from the at least two first offset images; a difference image generation process of generating a difference image between the second offset image and the immediately preceding offset image; and a subtraction process of subtracting the first offset image selected by the selection process and the difference image from the radiographic image.

According to another aspect of the present disclosure, there is provided a method for operating a radiographic image detection device including a pixel region in which a plurality of pixels detecting radiation are arranged and a reading unit that reads a pixel signal from the pixel region. The method comprises: a first offset image acquisition step of reading the pixel signal from the pixel region in a state in which the radiation is not emitted to acquire at least two first offset images having different accumulation times; a second offset image acquisition step of reading the pixel signal from the pixel region in an accumulation time shorter than that of the plurality of first offset images or using binning reading in a state in which the radiation is not emitted to acquire a second offset image; a reference image acquisition step of reading the pixel signal from the pixel region using the same reading method as that used for the second offset image and in a state in which gates of the pixels are turned off to acquire a reference image; a first dark current distribution image acquisition step of calculating a difference between the two first offset images having different accumulation times to acquire a first dark current distribution image; a second dark current distribution image acquisition step of calculating a difference between the second offset image and the reference image to acquire a second dark current distribution image; and a determination step of determining whether or not the first offset image and the second offset image need to be reacquired on the basis of a correction error of a corrected image obtained by correcting the first dark current distribution image on the basis of the second dark current distribution image.

According to yet another aspect of the present disclosure, there is provided an operation program for operating a radiographic image detection device comprising a pixel region in which a plurality of pixels detecting radiation are arranged, a reading unit that reads a pixel signal from the pixel region, and at least one processor. The operation program causes the processor to perform: a first offset image acquisition process of reading the pixel signal from the pixel region in a state in which the radiation is not emitted to acquire at least two first offset images having different accumulation times; a second offset image acquisition process of reading the pixel signal from the pixel region in an accumulation time shorter than that of the plurality of first offset images or using binning reading in a state in which the radiation is not emitted to acquire a second offset image; a reference image acquisition process of reading the pixel signal from the pixel region using the same reading method as that used for the second offset image and in a state in which gates of the pixels are turned off to acquire a reference image; a first dark current distribution image acquisition process of calculating a difference between the two first offset images having different accumulation times to acquire a first dark current distribution image; a second dark current distribution image acquisition process of calculating a difference between the second offset image and the reference image to acquire a second dark current distribution image; and a determination process of determining whether or not the first offset image and the second offset image need to be reacquired on the basis of a correction error of a corrected image obtained by correcting the first dark current distribution image on the basis of the second dark current distribution image.

According to the technique of the present disclosure, it is possible to provide a radiographic image detection device that can determine whether or not an offset image acquired during calibration needs to be reacquired, a method for operating the radiographic image detection device, and a program for operating the radiographic image detection device.

BRIEF DESCRIPTION OF THE DRAWINGS

Exemplary embodiments according to the technique of the present disclosure will be described in detail based on the following figures, wherein.

DETAILED DESCRIPTION

Figure 1:
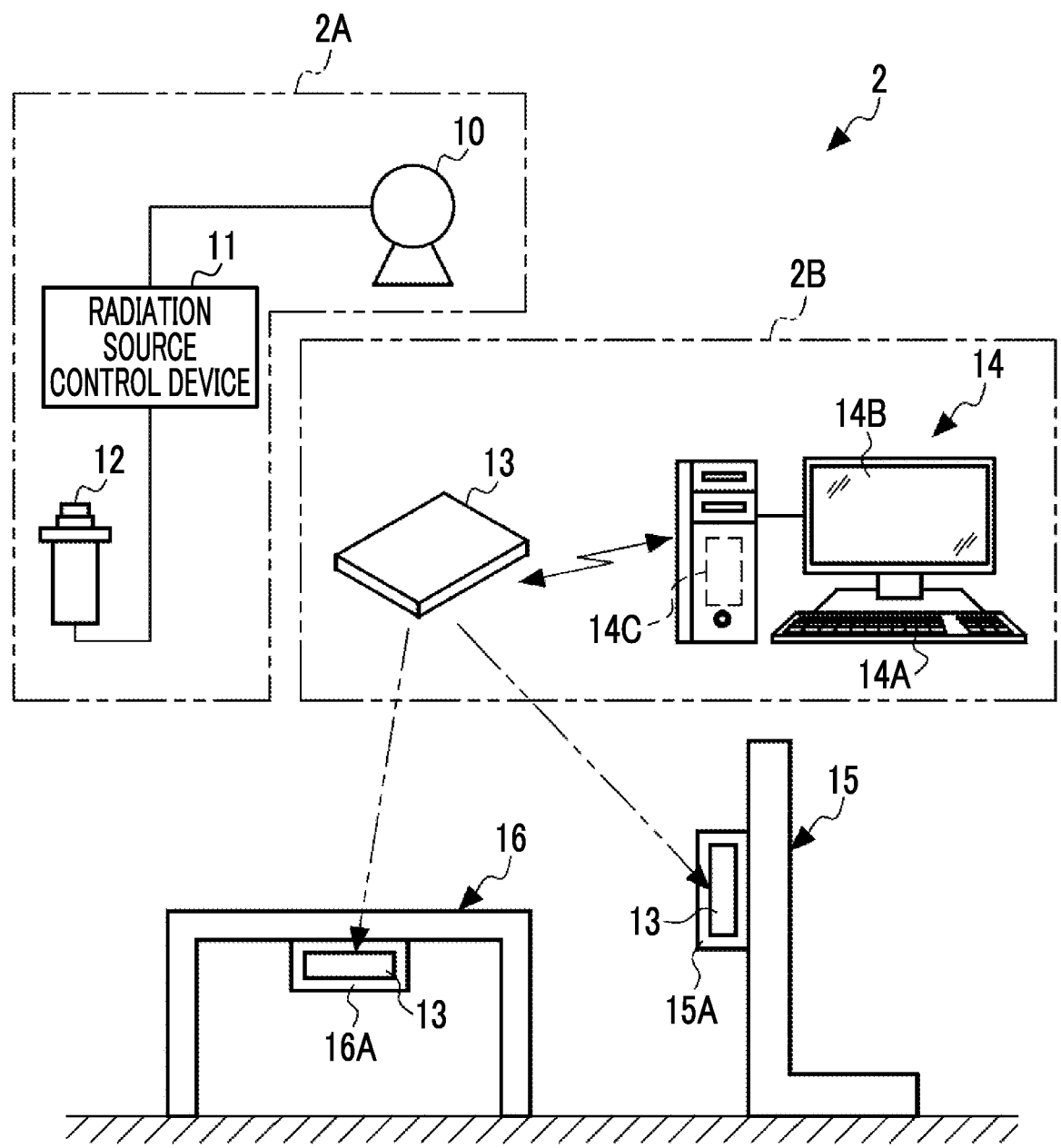
FIG. 1 is a schematic diagram illustrating a configuration of an X-ray imaging system.

In FIG. 1, an X-ray imaging system 2 includes an X-ray generation apparatus 2A and an X-ray imaging apparatus 2B. The X-ray generation apparatus 2A has an X-ray source 10, a radiation source control device 11, and an irradiation switch 12. The radiation source control device 11 controls the operation of the X-ray source 10. The irradiation switch 12 instructs the X-ray source 10 to start warm-up and irradiation with X-rays in response to an operation of an operator such as a radiology technician. In addition, the X-ray is an example of "radiation" according to the technology of the present disclosure.

The X-ray imaging apparatus 2B has an electronic cassette 13 and a console 14. The electronic cassette 13 is a portable X-ray image detection device. The console 14 controls the operation of the electronic cassette 13 and processes the display of an X-ray image. Further, the X-ray imaging system 2 is provided with, for example, an upright imaging stand 15 or a decubitus imaging stand 16. The upright imaging stand 15 is used in a case in which an image of the subject in an upright posture is captured. The decubitus imaging stand 16 is used in a case in which an image of the subject in a decubitus posture is captured. The electronic cassette 13 is set so as to be attachable to and detachable from a holder 15A of the upright imaging stand 15 or a holder 16A of the decubitus imaging stand 16. In addition, the X-ray image is an example of a "radiographic image" according to the technology of the present disclosure. Further, the electronic cassette 13 is an example of a "radiographic image detection device" according to the technology of the present disclosure.

Further, the X-ray imaging system 2 is provided with a radiation source movement device (not illustrated) that is used by the operator to move the X-ray source 10 in a desired direction and position. The radiation source movement device makes it possible to move the X-ray source 10 according to the imaging stand used for X-ray imaging. The operator can move the X-ray source 10 so as to face the upright imaging stand 15 or the decubitus imaging stand 16.

The X-ray generation apparatus 2A and the X-ray imaging apparatus 2B are not electrically connected to each other. That is, the X-ray imaging apparatus 2B is not a synchronous type that operates the electronic cassette 13 in synchronization with the start of irradiation with X-rays, but is an asynchronous type. Therefore, the electronic cassette 13 has an irradiation start detection function of detecting the start of irradiation with X-rays by the X-ray generation apparatus 2A.

As is well known, the X-ray source 10 includes an X-ray tube and an irradiation field limiter (collimator) that limits an irradiation field of X-rays emitted by the X-ray tube. The X-ray tube has a cathode which is a filament emitting thermoelectrons and an anode (target) which collides with the thermoelectrons emitted from the cathode and emits X-rays. In a case in which the X-ray source 10 receives an instruction to start warm-up, it starts preheating the filament and rotating the anode. The warm-up ends in a case in which the preheating of the filament is completed and the anode reaches a prescribed number of rotations.

The console 14 is connected to the electronic cassette 13 by a wired method or a wireless method so as to communicate therewith. The console 14 controls the operation of the electronic cassette 13 in response to an input operation of the operator through an input device 14A such as a keyboard. The X-ray image acquired by the electronic cassette 13 is displayed on a display 14B that is provided in the console 14. In addition, the X-ray image is stored in a storage device 14C, such as a hard disk or a flash memory provided in the console 14, or an image storage server (not illustrated) that is connected to the console 14 by a network.

Figure 2:
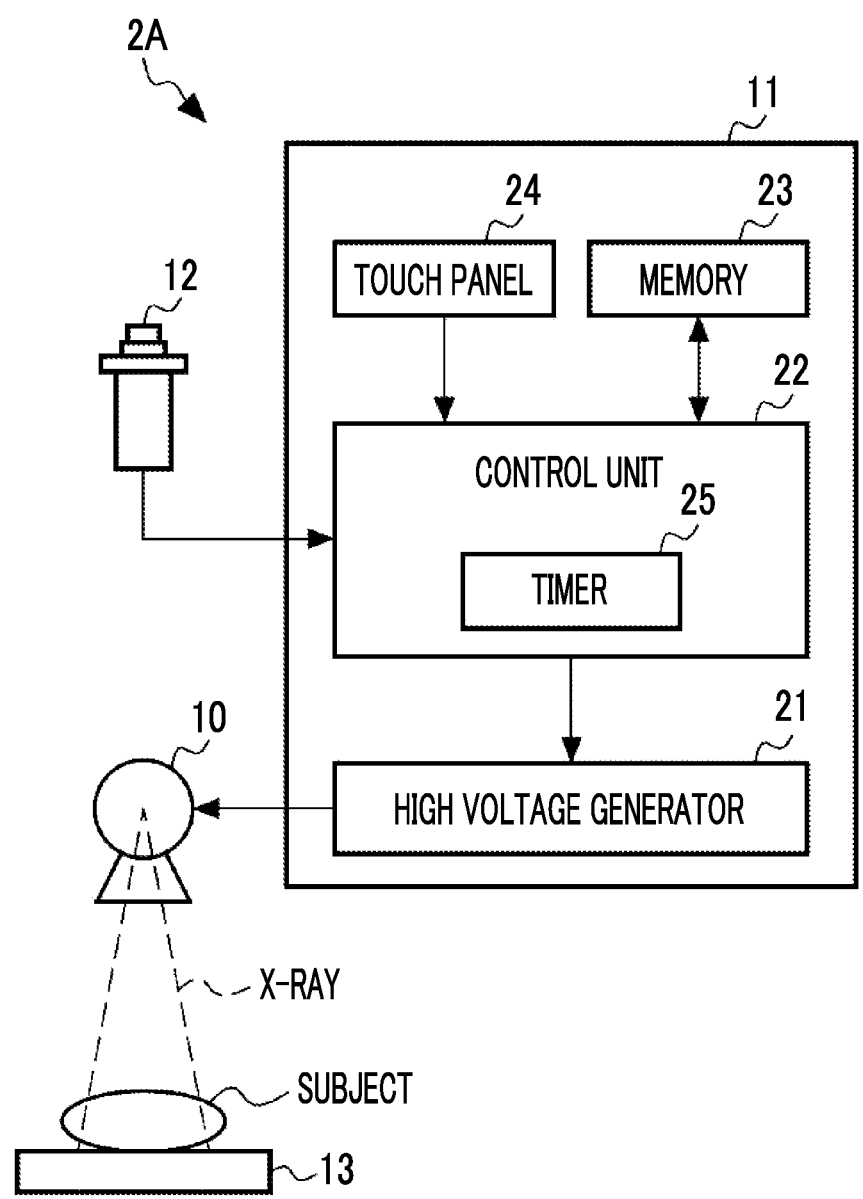
FIG. 2 is a schematic diagram illustrating a configuration of an X-ray generation apparatus.

In FIG. 2, the radiation source control device 11 includes a high voltage generator 21, a control unit 22, a memory 23, and a touch panel 24. The high voltage generator 21 boosts an input voltage with a transformer to generate a high voltage. The high voltage generated by the high voltage generator 21 is supplied as a tube voltage to the X-ray source 10 through a high voltage cable. The control unit 22 controls the tube voltage and a tube current supplied to the X-ray source 10 and an X-ray irradiation time.

The irradiation switch 12, the high voltage generator 21, the memory 23, and the touch panel 24 are connected to the control unit 22. The irradiation switch 12 is a switch that inputs an instruction to the control unit 22. The irradiation switch 12 is configured such that it can be pressed in two steps. In a case in which the irradiation switch 12 is pressed in one step (hereinafter, referred to as "halfway"), the control unit 22 outputs a warm-up instruction signal to the high voltage generator 21 to direct the X-ray source 10 to start warm-up. Further, in a case in which the irradiation switch 12 is pressed in two steps (hereinafter, referred to as "fully"), the control unit 22 outputs an irradiation instruction signal to the high voltage generator 21 to direct the X-ray source 10 to start irradiation with X-rays.

Like the storage device 14C of the console 14, the memory 23 stores in advance several types of imaging conditions including irradiation conditions, such as a tube voltage, a tube current, and an irradiation time. The operator manually sets the imaging conditions through the touch panel 24. A plurality of types of imaging conditions read from the memory 23 are displayed on the touch panel 24. The operator selects the same imaging conditions as the imaging conditions input to the console 14 from the displayed imaging conditions to set the imaging conditions in the radiation source control device 11. The control unit 22 is provided with a timer 25 for stopping the irradiation with X-rays in a case in which the set irradiation time comes.

Figure 3:
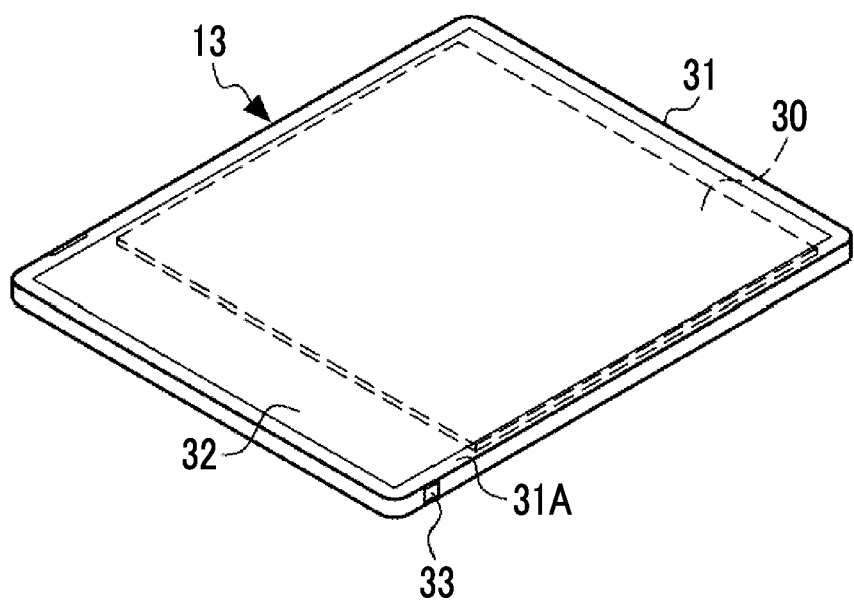
FIG. 3 is a perspective view illustrating an electronic cassette.

In FIG. 3, the electronic cassette 13 is an X-ray image detection device that detects X-rays transmitted through the subject and outputs an X-ray image. The electronic cassette 13 includes an image detection unit 30 and a housing 31. The housing 31 has a flat box shape and accommodates the image detection unit 30. The housing 31 is made of, for example, a conductive resin. In the housing 31, a rectangular opening is formed in a front surface 31A as an incident surface on which X-rays are incident, and an X-ray transmission plate 32 is attached to the opening. The X-ray transmission plate 32 is made of, for example, a carbon material that is lightweight and has high rigidity and high X-ray transparency.

The housing 31 also functions as an electromagnetic shield for preventing electromagnetic noise from entering the electronic cassette 13 and electromagnetic noise from being emitted from the electronic cassette 13 to the outside. In addition, a battery (for example, a secondary battery) that supplies power for driving the electronic cassette 13 and an antenna for performing wireless communication with the console 14 are provided in the housing 31.

For example, the housing 31 has a size conforming to the international standard ISO 4090:2001 which is substantially the same as that of a film cassette or an IP cassette. The electronic cassette 13 is set in the holder 15A of the upright imaging stand 15 or the holder 16A of the decubitus imaging stand 16 so as to be held in a posture in which the front surface 31A of the housing 31 faces the X-ray source 10. In addition, the electronic cassette 13 can be used in a state in which it is placed on the bed on which the subject lies supine, without using the upright imaging stand 15 and the decubitus imaging stand 16.

Figure 4:
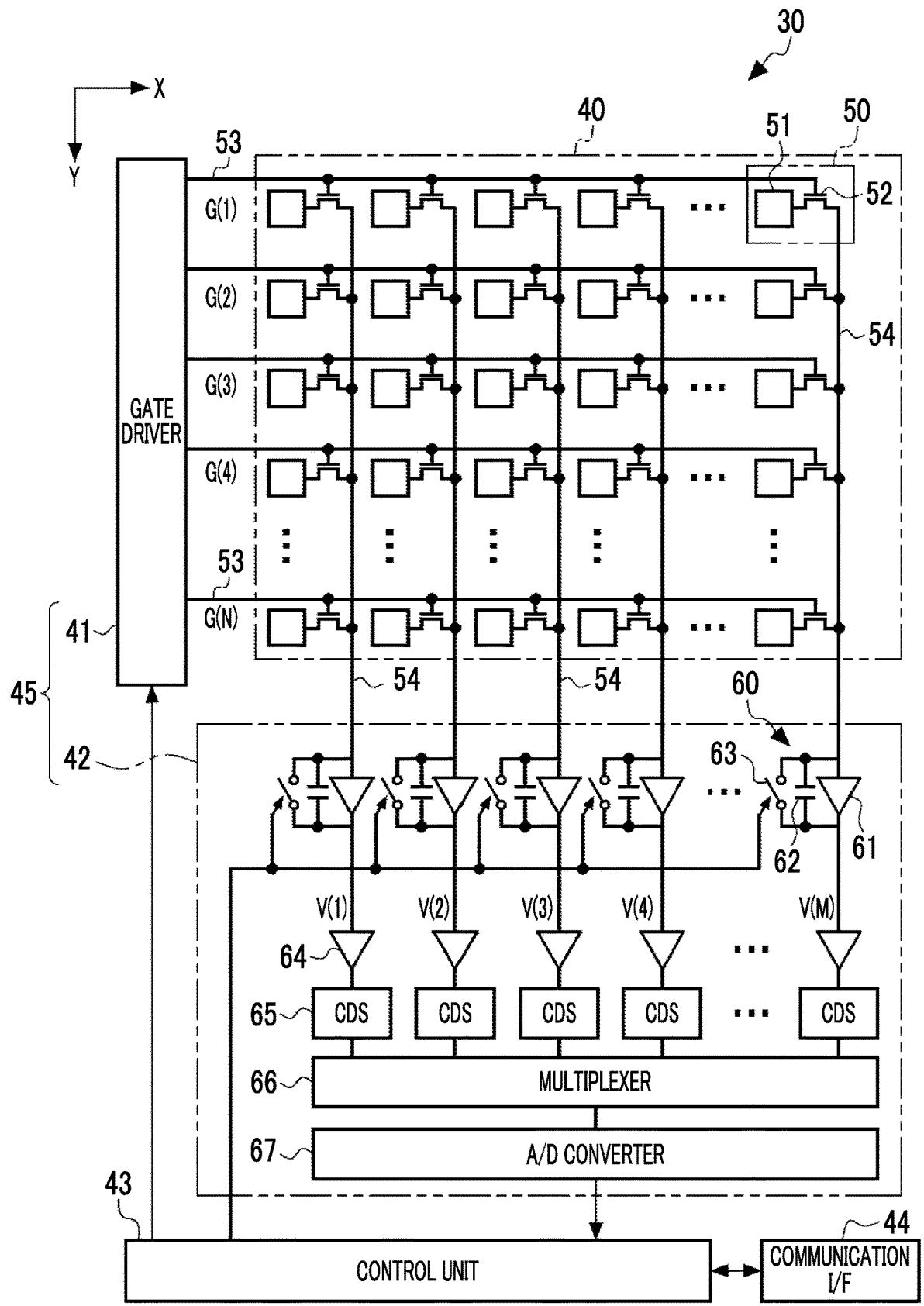
FIG. 4 is a diagram illustrating a configuration of an image detection unit.

In FIG. 4, the image detection unit 30 includes a pixel region 40, a gate driver 41, a signal processing circuit 42, a control unit 43, and a communication interface (I/F) 44. The gate driver 41 and the signal processing circuit 42 form a reading unit 45 that reads a pixel signal from the pixel region 40. The gate driver 41 and the signal processing circuit 42 are an example of a "reading unit" according to the technology of the present disclosure.

The pixel region 40 is formed on a thin film transistor (TFT) active matrix substrate. The pixel region 40 includes a plurality of pixels 50 that are arranged in a matrix along the X direction and the Y direction which are orthogonal to each other. It is assumed that the number of pixels 50 arranged in the X direction is M and the number of pixels 50 arranged in the Y direction is N. Each of N and M is an integer that is equal to or greater than 2. For example, each of N and M is about 2000. The array pattern of the pixels 50 is not limited to a square array, and may be a non-square array such as a so-called honeycomb array. The pixel 50 is an element that generates and accumulates charge according to the amount of incident X-rays.

The pixel region 40 is provided with a scintillator (not illustrated) that converts X-rays into visible light. The image detection unit 30 is an indirect conversion type in which photoelectric conversion is performed on the visible light converted by the scintillator in each pixel 50. The scintillator is made of, for example, CsI:Tl (thallium-activated cesium iodide) or $Gd_2O_2S$:Tb (terbium-activated gadolinium oxysulfide) and is disposed so as to face the entire surface of the pixel region 40. The image detection unit 30 is, for example, a penetration side sampling (PSS) type in which the scintillator and the TFT active matrix substrate are disposed in this order from an X-ray incident side. Further, the image detection unit 30 may be an irradiation side sampling (ISS) type in which the TFT active matrix substrate and the scintillator are disposed in this order from the X-ray incident side.

The image detection unit 30 is not limited to the indirect conversion type, but may be a direct conversion type using a conversion layer (for example, amorphous selenium) that directly converts X-rays into charge.

The pixel 50 includes a photoelectric conversion unit 51 that performs photoelectric conversion on the visible light converted by the scintillator to generate charge and accumulates the charge and a TFT 52 as a switching element. The photoelectric conversion unit 51 includes, for example, a p-intrinsic-n (PIN) semiconductor layer, an upper electrode that is disposed above the semiconductor layer, and a lower electrode that is disposed below the semiconductor layer. A bias voltage is applied to the upper electrode. The lower electrode is connected to the TFT 52.

The pixel region 40 includes N scanning lines 53 that extend in the X direction and M signal lines 54 that extend in the Y direction. The N scanning lines 53 and the M signal lines 54 are wired in a grid shape. Each pixel 50 is connected to an intersection portion of the scanning line 53 and the signal line 54. Specifically, in the pixel 50, a gate electrode of the TFT 52 is connected to the scanning line 53 and a source electrode of the TFT 52 is connected to the signal line 54. A drain electrode of the TFT 52 is connected to the photoelectric conversion unit 51.

Each scanning line 53 is commonly connected to M pixels 50 corresponding to one pixel row. Each signal line 54 is commonly connected to N pixels 50 corresponding to one pixel column. Each scanning line 53 is connected to the gate driver 41. Each signal line 54 is connected to the signal processing circuit 42.

The gate driver 41 outputs a gate pulse G(n) as a scanning signal to an n-th scanning line 53. Here, n is an integer from 1 to N. The gate pulse G(n) is applied to the gate electrodes of the TFTs 52 connected to the n-th scanning line 53. The TFT 52 is turned on in a case in which the voltage of the gate pulse G(n) is at a high level and is turned off in a case in which the voltage is at a low level. The time when the TFT 52 is turned on is defined by the width of the gate pulse G(n).

The charge accumulated in the photoelectric conversion unit 51 of the pixel 50 is output to the signal processing circuit 42 through the signal line 54 in a case in which the TFT 52 is turned on.

The signal processing circuit 42 includes an integrator 60 as a charge amplifier, an amplifier 64, a correlated double sampling (CDS) circuit 65, a multiplexer 66, and an analog/digital (A/D) converter 67. The integrator 60 is individually connected to each signal line 54. Each integrator 60 includes an operational amplifier 61, a capacitor 62, and a reset switch 63. The capacitor 62 and the reset switch 63 are connected in parallel between an input terminal and an output terminal of the operational amplifier 61. The signal line 54 is connected to the input terminal of the operational amplifier 61.

The integrator 60 integrates the charge input from the signal line 54, converts an integrated value into an analog voltage signal V(k), and outputs the analog voltage signal V(k). Here, k is an integer from 1 to M. The analog voltage signal V(k) corresponds to the integrated value of the charge input from a k-th signal line 54 to the integrator 60.

The output terminal of the operational amplifier 61 of each pixel column is connected to the input side of the multiplexer 66 through the amplifier 64 and the CDS circuit 65. The A/D converter 67 is connected to the output side of the multiplexer 66. The CDS circuit 65 has a sample-and-hold circuit. The CDS circuit 65 performs correlated double sampling on the analog voltage signal V(k) to remove a reset noise component.

The multiplexer 66 sequentially selects the connected M CDSs 65 and sequentially inputs the analog voltage signal V(k) subjected to the correlated double sampling to the A/D converter 67. In addition, the amplifier 64 is not limited to the configuration in which it is provided between the integrator 60 and the CDS circuit 65, but may be provided between the CDS circuit 65 and the A/D converter 67.

The A/D converter 67 sequentially converts the analog voltage signal V(k) input from the multiplexer 66 into a digital value and outputs the digital value as a pixel signal to the control unit 43. That is, the pixel signal is a signal corresponding to the amount of incident X-rays read from the pixel region 40 by the reading unit 45. The pixel signals corresponding to one frame which have been read from each pixel 50 of the pixel region 40 form an X-ray image.

The control unit 43 controls the operation of the reading unit 45 reading the pixel signal from the pixel region 40 to perform an X-ray imaging process, and performs a process of generating an X-ray image based on the read pixel signal. Further, the control unit 43 performs a calibration process of acquiring an offset image in a state in which no X-rays are emitted and a correction process of correcting the X-ray image on the basis of the acquired offset image, which will be described in detail below. Furthermore, the control unit 43 performs the above-mentioned irradiation start detection process.

The communication I/F 44 is connected to the console 14 (see FIG. 1) wirelessly or in a wired manner, and transmits and receives data to and from the console 14. For example, the communication I/F 44 receives data including imaging conditions transmitted from the console 14 and transmits data indicating the X-ray image generated by the control unit 43 to the console 14. The imaging conditions include the irradiation time determined corresponding to, for example, an imaging part.

Figure 5:
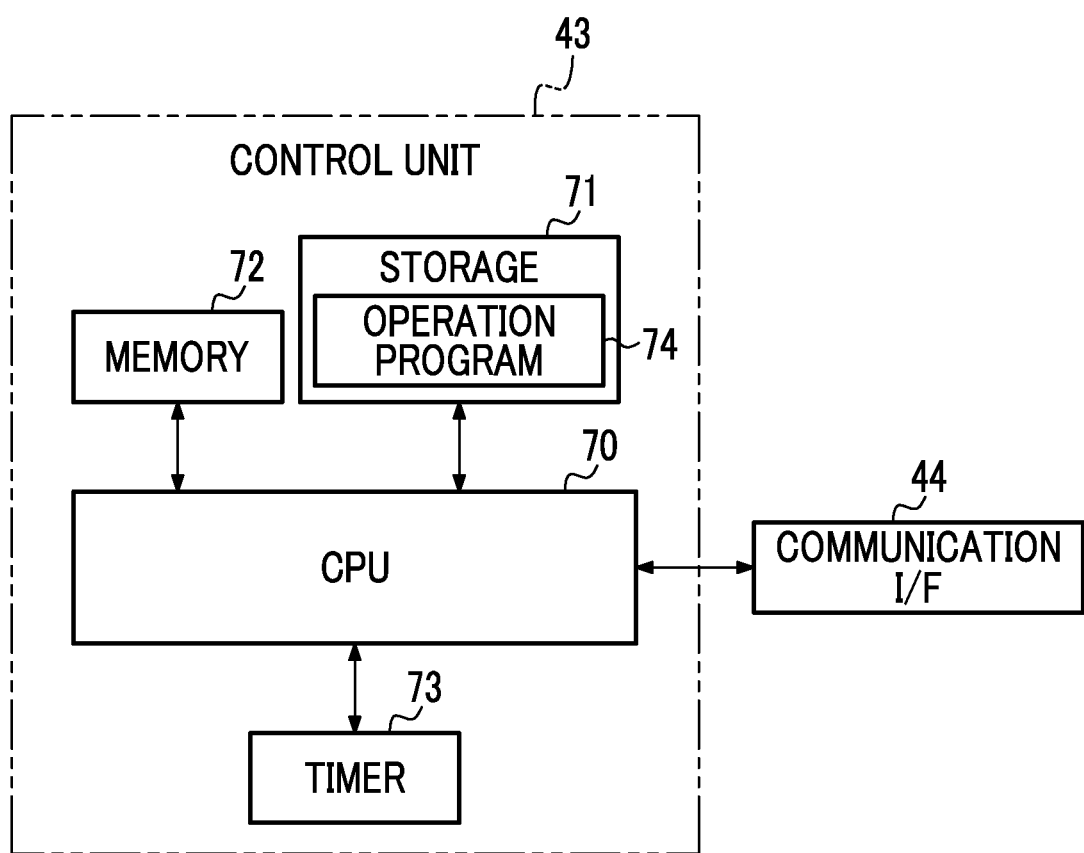
FIG. 5 is a block diagram illustrating a configuration of a control unit.

In FIG. 5, the control unit 43 of the image detection unit 30 includes, for example, a central processing unit (CPU) 70, a storage 71, a memory 72, and a timer 73. The storage 71 stores an operation program 74 and various kinds of data. The storage 71 is a non-volatile storage device such as a flash memory. The memory 72 is a volatile storage device, such as a random access memory (RAM) and is used as a work memory. The timer 73 is a timing device that measures time such as the irradiation time. The CPU 70 operates each unit on the basis of the operation program 74 to implement various functions. The CPU 70 is an example of a "processor" according to the technology of the present disclosure.

Figure 6:
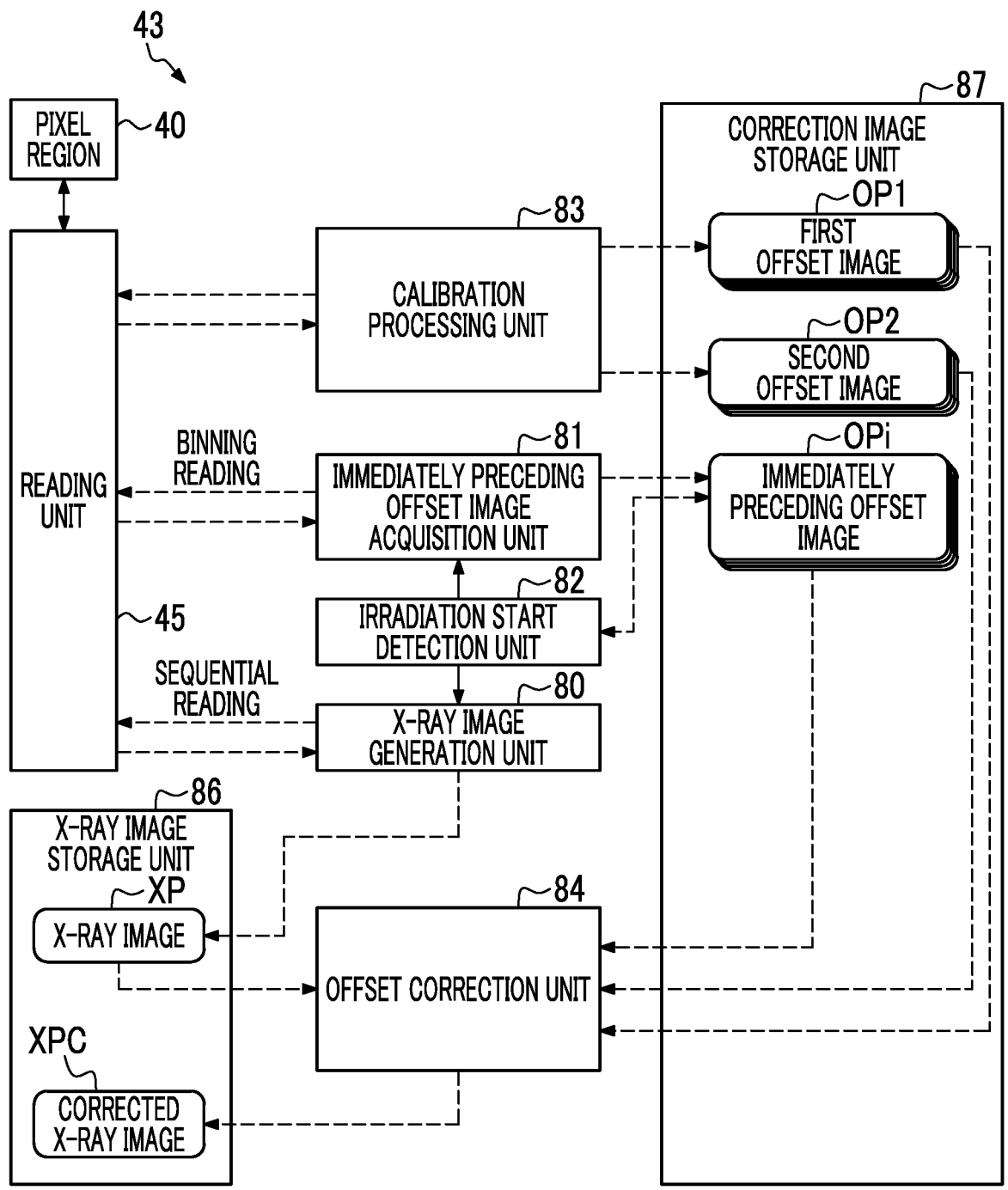
FIG. 6 is a block diagram illustrating functions implemented by the control unit.

FIG. 6 illustrates various functional units that are implemented in the control unit 43 by the CPU 70. In FIG. 6, an X-ray image generation unit 80, an immediately preceding offset image acquisition unit 81, an irradiation start detection unit 82, a calibration processing unit 83, and an offset correction unit 84 are implemented in the control unit 43. Each of an X-ray image storage unit 86 and a correction image storage unit 87 is implemented using the storage 71 and/or the memory 72.

Figure 7:
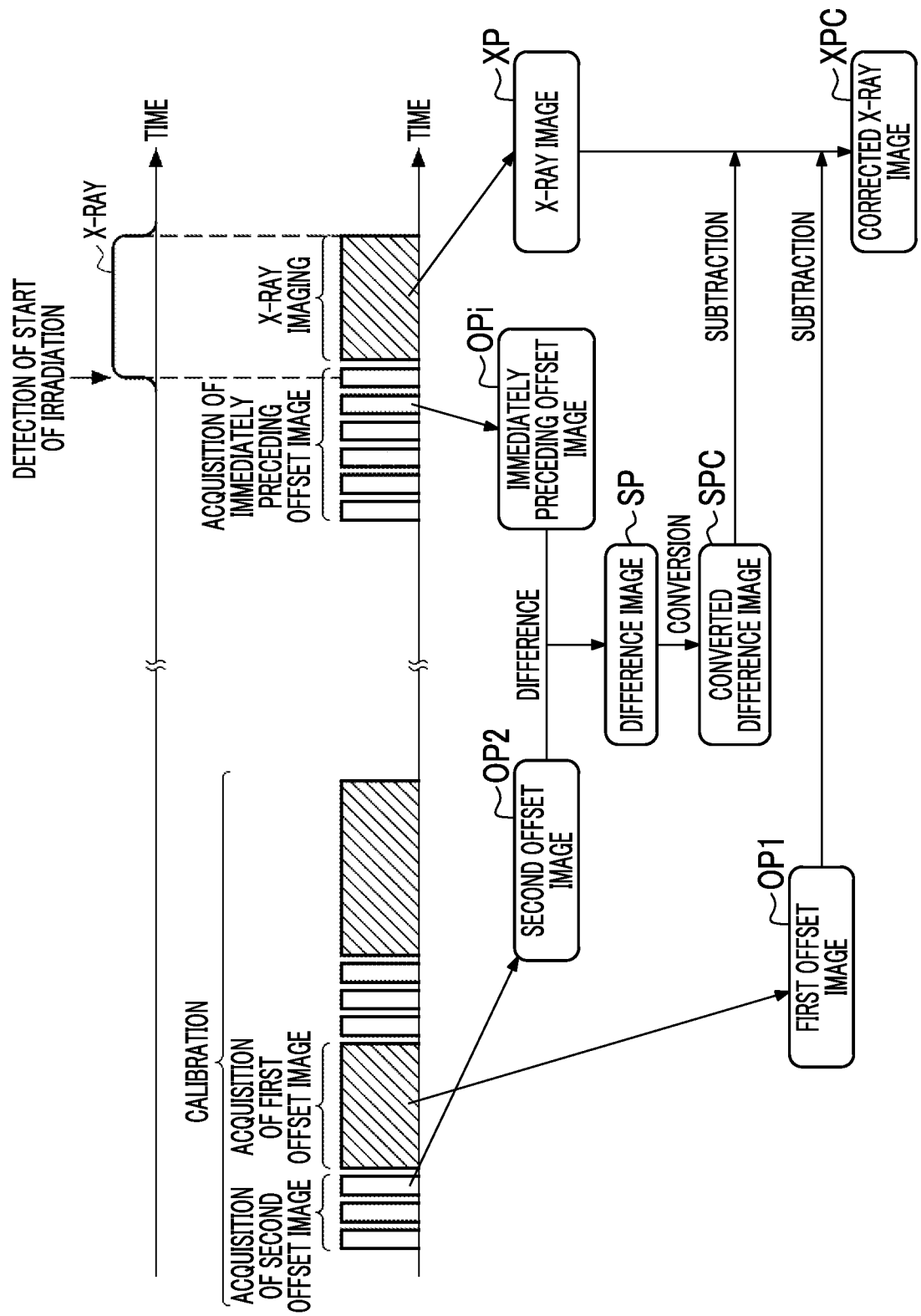
FIG. 7 is a schematic diagram illustrating the outline of a process performed by the control unit.

As illustrated in FIG. 7, the X-ray image generation unit 80 operates during X-ray imaging that is performed in a state in which X-rays are emitted. After the pixel region 40 is irradiated with the X-rays generated by the X-ray generation apparatus 2A through the subject, the X-ray image generation unit 80 drives the reading unit 45 to read pixel signals from the pixel region 40. Then, the X-ray image generation unit 80 generates an X-ray image XP on the basis of the read pixel signals. That is, the X-ray image generation unit 80 performs an X-ray image generation process.

Figure 8:
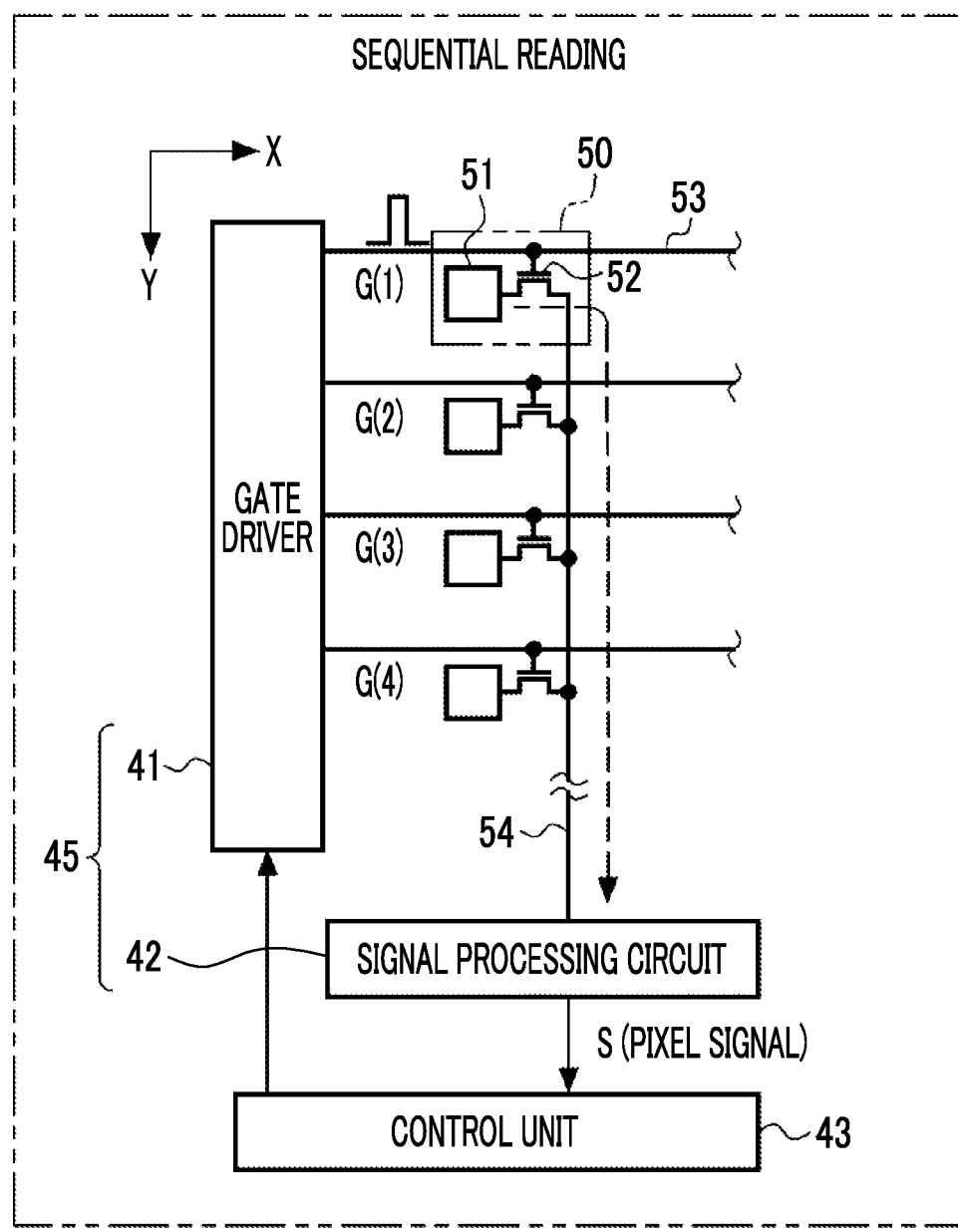
FIG. 8 is a diagram illustrating a sequential reading method.

The X-ray image generation unit 80 drives the reading unit 45 using a "sequential reading method" which sequentially selects the scanning lines 53 and individually reads the charge accumulated in each pixel 50 included in the pixel region 40. As illustrated in FIG. 8, in the sequential reading method, the gate driver 41 sequentially applies the gate pulse to the N scanning lines 53 to sequentially select the scanning lines 53 and reads charge from the pixels 50 connected to the selected scanning line 53.

In the sequential reading method, the TFTs 52 connected to one scanning line 53, to which the gate pulse has been applied, are turned on, and charge is output from the photoelectric conversion units 51 connected to the TFTs 52 to the signal line 54. The charge output to the signal line 54 is subjected to signal processing by the signal processing circuit 42 and is input as a pixel signal S to the control unit 43. The X-ray image generation unit 80 generates the X-ray image XP on the basis of the pixel signals S corresponding to all of the pixels 50 included in the pixel region 40. The X-ray image generation unit 80 stores the generated X-ray image XP in the X-ray image storage unit 86.

As illustrated in FIG. 7, the immediately preceding offset image acquisition unit 81 operates immediately before the X-ray imaging. The immediately preceding offset image acquisition unit 81 drives the reading unit 45 in a state in which the pixel region 40 is not irradiated with the X-rays immediately before the X-ray imaging to read the pixel signals from the pixel region 40. Then, the immediately preceding offset image acquisition unit 81 generates an immediately preceding offset image OPi on the basis of the read pixel signals. That is, the immediately preceding offset image acquisition unit 81 performs an immediately preceding offset image acquisition process. In addition, the immediately preceding offset image acquisition unit 81 repeatedly performs the immediately preceding offset image acquisition process a plurality of times to acquire a plurality of immediately preceding offset images OPi immediately before the X-ray imaging. The immediately preceding offset image acquisition unit 81 stores the plurality of acquired immediately preceding offset images OPi in the correction image storage unit 87.

Figure 9:
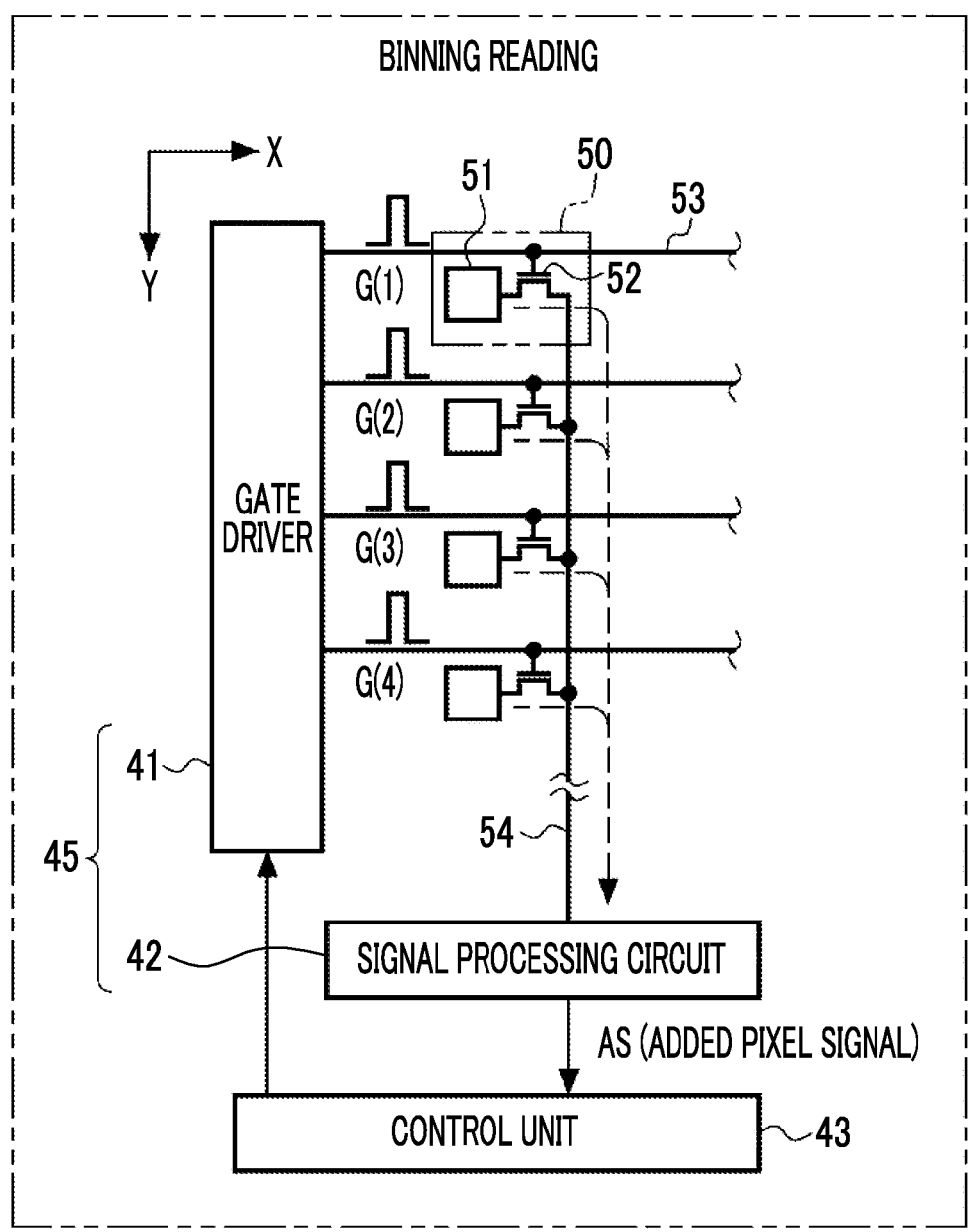
FIG. 9 is a diagram illustrating a binning reading method.

The immediately preceding offset image acquisition unit 81 drives the reading unit 45 using a "binning reading method" that simultaneously selects a plurality of scanning lines 53 adjacent to each other, adds the charge accumulated in a plurality of pixels 50 included in the pixel region 40, and reads the added charge. As illustrated in FIG. 9, in the binning reading method, the N scanning lines 53 are divided into sets of four scanning lines 53, and the gate driver 41 simultaneously applies the gate pulse to each set of four scanning lines 53, adds charge corresponding to four pixels, and reads the added charge. In addition, the number of pixels added by the binning reading is not limited to four pixels.

In the binning reading method, the TFTs 52 connected to the plurality of scanning lines 53, to which the gate pulses have been applied, are turned on, and charge is output from the photoelectric conversion units 51 connected to the TFTs 52 to the signal lines 54. A plurality of charges output from a plurality of pixels 50 connected to the same signal line 54 are added on the signal line 54 and are then input to the signal processing circuit 42. The charge input to the signal processing circuit 42 is subjected to signal processing and is input as an added pixel signal AS to the control unit 43. The immediately preceding offset image acquisition unit 81 generates the immediately preceding offset image OPi on the basis of the added pixel signal AS corresponding to each addition pixel included in the pixel region 40. In addition, the addition pixels indicate a plurality of pixels 50 from which charge is added. In this embodiment, as illustrated in FIG. 9, four pixels 50 arranged in the Y direction are the addition pixels.

Figure 10:
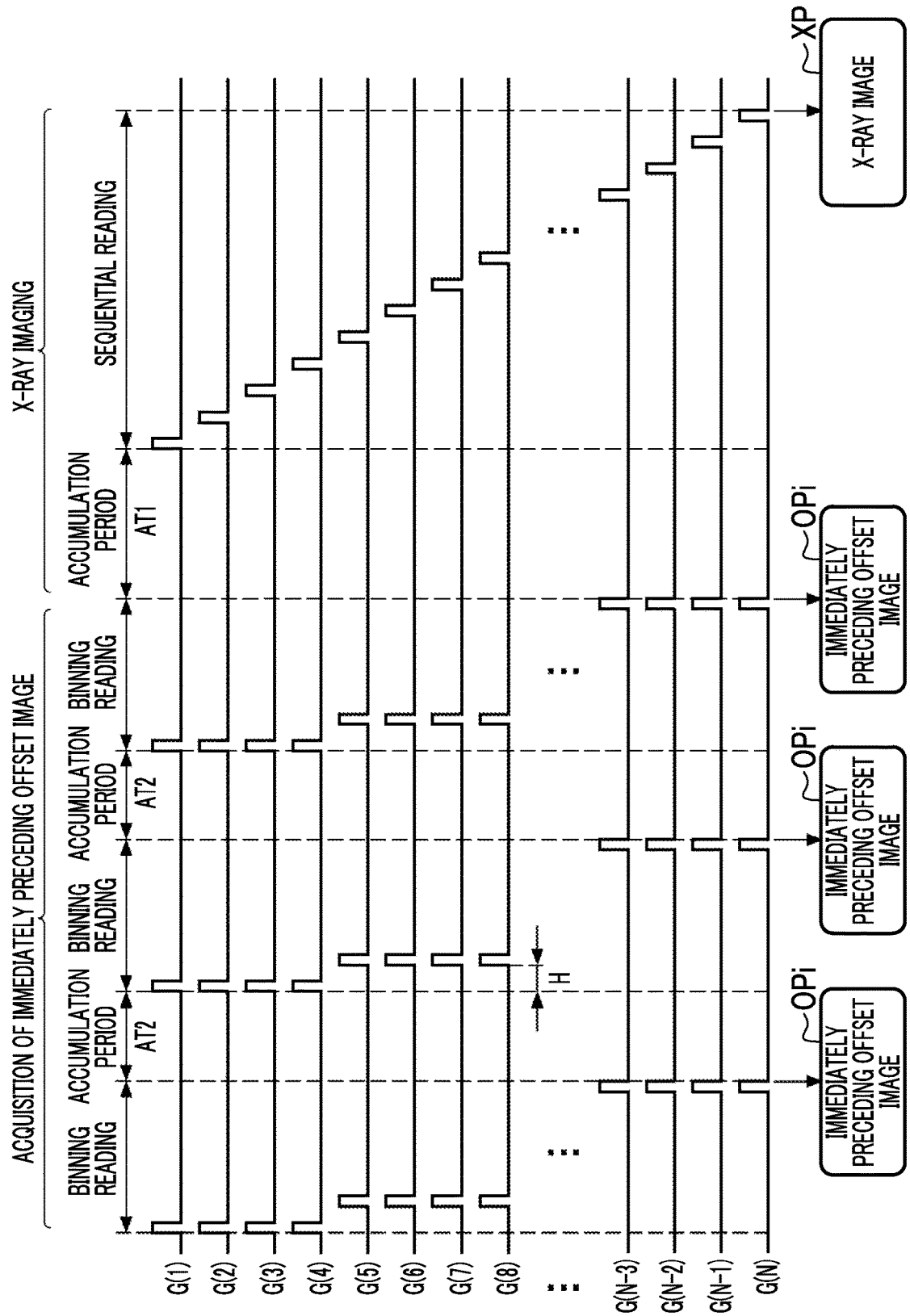
FIG. 10 is a timing chart illustrating the timing of gate pulses during X-ray imaging.

As illustrated in FIG. 10, in the sequential reading performed during the X-ray imaging, the scanning lines 53 are sequentially selected one by one. In contrast, in the binning reading performed during the acquisition of the immediately preceding offset image, the scanning lines 53 are sequentially selected four by four. Therefore, in this embodiment, the read time in the binning reading method is about one fourth of the read time in the sequential reading method.

Further, since the operation of the immediately preceding offset image acquisition unit 81 acquiring the immediately preceding offset image OPi is performed immediately before the X-ray imaging, it also functions as a reset operation of discarding the charge accumulated in the pixel region 40 immediately before the X-ray imaging. Therefore, a charge accumulation period (hereinafter, simply referred to as an "accumulation period") AT1 in the X-ray imaging corresponds to a period from the end of the binning reading immediately before the X-ray imaging to the start of the sequential reading. During the accumulation period AT1, charge corresponding to the amount of X-rays emitted is mainly accumulated in the pixel region 40.

In the operation of acquiring the immediately preceding offset image OPi, the binning reading is periodically repeated. Therefore, an accumulation period AT2 in the operation of acquiring the immediately preceding offset image OPi corresponds to a period from the end of the binning reading to the start of the next binning reading. During the accumulation period AT2, the charge caused by the dark current generated in each pixel 50 is mainly accumulated in the pixel region 40. The dark current is a noise component that is generated in a state in which no X-rays are emitted and is mainly caused by heat. In addition, during the accumulation period AT1, in addition to the charge corresponding to the amount of X-rays emitted, the charge caused by the dark current is accumulated in the pixel region 40.

The accumulation period AT2 may have the same length as the accumulation period AT1. However, in this embodiment, the accumulation period AT2 is set to be shorter than the accumulation period AT1 in order to shorten the acquisition time of the immediately preceding offset image OPi (that is, AT2<AT1). In this embodiment, since the pixel signal is read by the binning reading method during the operation of acquiring the immediately preceding offset image OPi, the immediately preceding offset image OPi can be acquired in a shorter time than the X-ray image XP. Furthermore, since AT2<AT1 is satisfied, the immediately preceding offset image OPi can be acquired in a shorter time.

Figure 11:
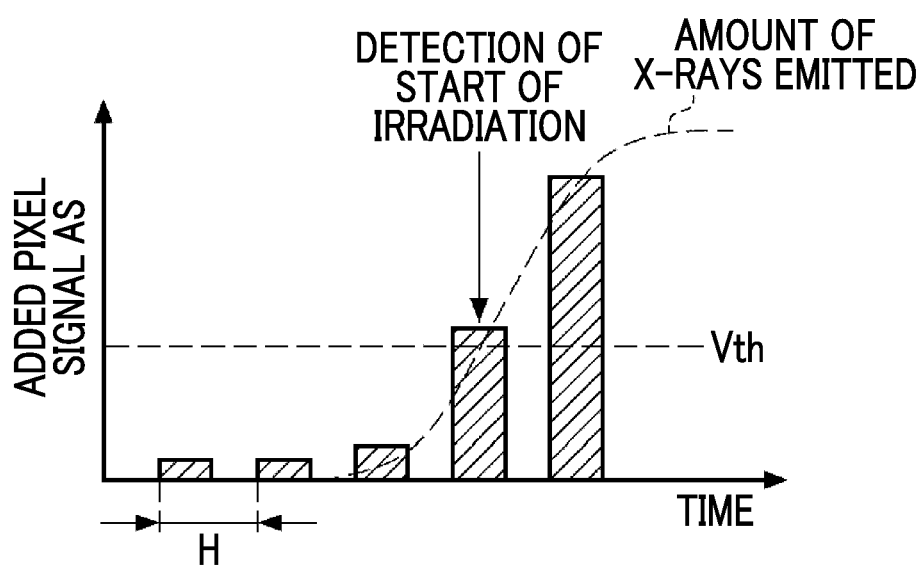
FIG. 11 is a diagram illustrating an irradiation start determination process.

Returning to FIG. 6, the irradiation start detection unit 82 detects that the X-ray generation apparatus 2A has started irradiation with X-rays on the basis of the immediately preceding offset image OPi acquired by the immediately preceding offset image acquisition unit 81. Specifically, the irradiation start detection unit 82 monitors the signal value of the added pixel signal AS read by the binning reading in the operation of acquiring the immediately preceding offset image OPi, as illustrated in FIG. 11. The irradiation start detection unit 82 determines that irradiation with X-rays has been started in a case in which the signal value of the added pixel signal AS is equal to or greater than a threshold value Vth. For example, the irradiation start detection unit 82 performs irradiation start detection every selection switching time H of the scanning line 53 (see FIG. 10). The selection switching time H is the time interval of the gate pulse output from the gate driver 41.

For example, the irradiation start detection unit 82 performs the irradiation start detection on the basis of the added pixel signal AS obtained through one signal line 54. In addition, the irradiation start detection unit 82 may perform the irradiation start detection on the basis of the maximum value of the added pixel signals AS obtained through a plurality of signal lines 54 for each pixel row. Further, the irradiation start detection unit 82 may perform the irradiation start detection on the basis of an average value or a sum, instead of the maximum value of the added pixel signals AS for each pixel row. Furthermore, the irradiation start detection unit 82 may perform the irradiation start detection on the basis of a difference value between the added pixel signals AS acquired every selection switching time H.

In a case in which the start of irradiation with X-rays has been detected, the irradiation start detection unit 82 notifies the immediately preceding offset image acquisition unit 81 and the X-ray image generation unit 80 that the start of irradiation has been detected. In a case in which the notification is received from the irradiation start detection unit 82, the immediately preceding offset image acquisition unit 81 stops the binning reading after the binning reading is performed on the final scanning line 53. In a case in which the notification is received from the irradiation start detection unit 82, the X-ray image generation unit 80 starts the measurement of the irradiation time from the time when the binning reading is stopped with the timer 73 (see FIG. 5). The irradiation time is a value that is included in the imaging conditions acquired by the control unit 43 from the console 14. The X-ray image generation unit 80 starts the sequential reading in a case in which the irradiation time has elapsed. The irradiation period corresponds to the accumulation period AT1.

The calibration processing unit 83 acquires a first offset image OP1 and a second offset image OP2 in a state in which no X-rays are emitted during calibration such as in a case in which the electronic cassette 13 is started up or during maintenance. As illustrated in FIG. 7, the first offset image OP1 and the second offset image OP2 are acquired before the X-ray imaging and the acquisition of the immediately preceding offset image OPi. For example, calibration is automatically performed in a case in which the electronic cassette 13 is started up, regardless of the operation of the operator. In addition, the calibration may be performed according to the operation of the operator.

Figure 12:
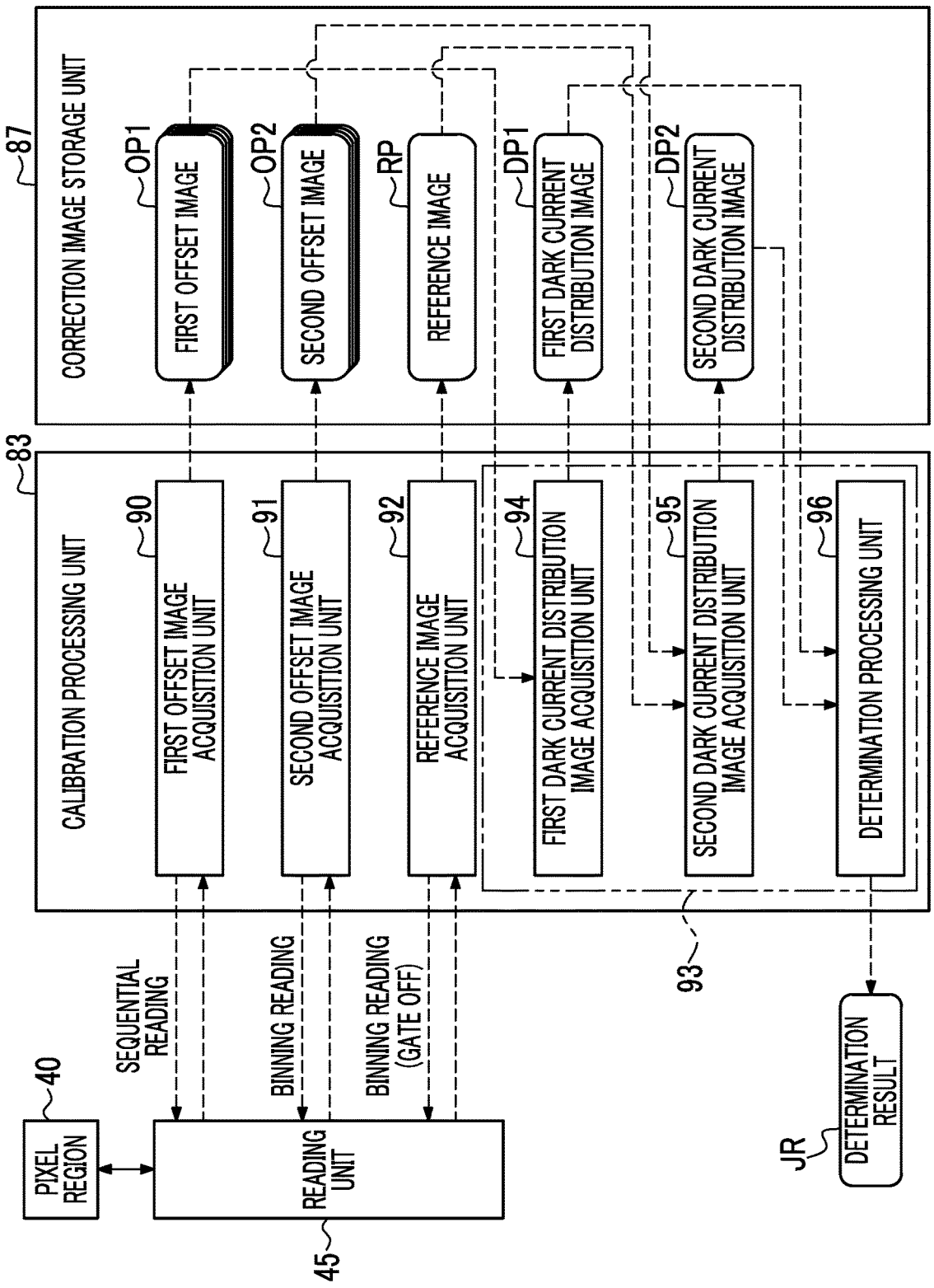
FIG. 12 is a block diagram illustrating a functional configuration of a calibration processing unit.

As illustrated in FIG. 12, the calibration processing unit 83 includes a first offset image acquisition unit 90, a second offset image acquisition unit 91, a reference image acquisition unit 92, and a determination unit 93. The process of each of the units is performed during the calibration.

The first offset image acquisition unit 90 performs a first offset image acquisition process of acquiring the first offset image OP1 using the same reading method (that is, the sequential reading method) as that used for the X-ray image XP. The second offset image acquisition unit 91 performs a second offset image acquisition process of acquiring the second offset image OP2 using the same reading method (that is, the binning reading method) as that used for the immediately preceding offset image OPi.

Figure 13:
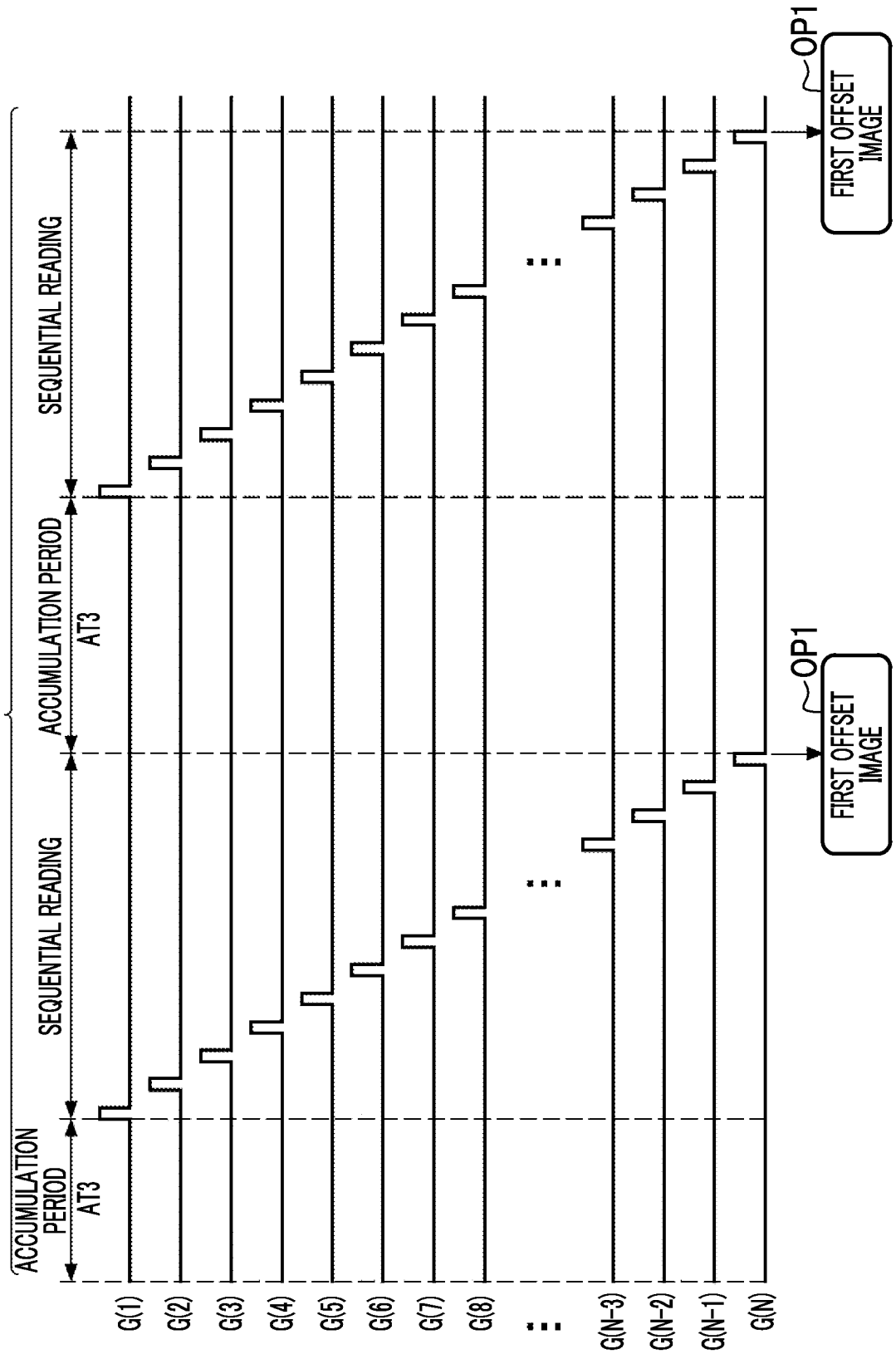
FIG. 13 is a timing chart illustrating the timing of the gate pulses in a case in which a first offset image is acquired.

As illustrated in FIG. 13, unlike the X-ray image generation unit 80, the first offset image acquisition unit 90 drives the reading unit 45 in a state in which no X-rays are emitted. Except this configuration, the first offset image acquisition unit 90 drives the reading unit 45 using the same driving method as the X-ray image generation unit 80. In addition, the first offset image acquisition unit 90 acquires a plurality of first offset images OP1 by performing the sequential reading a plurality of times while changing the length (accumulation time) of an accumulation period AT3. The first offset image acquisition unit 90 may acquire at least two first offset images OP1 having different accumulation times.

The first offset image acquisition unit 90 stores the plurality of acquired first offset images OP1 in the correction image storage unit 87 (see FIG. 12). Among the plurality of first offset images OP1 stored in the correction image storage unit 87, the first offset image OP1 having the accumulation period AT3 whose length is equal or similar to the length of the accumulation period AT1 during the X-ray imaging is selected by the offset correction unit 84 and is used for offset correction, which will be described in detail below. Further, among the plurality of first offset images OP1 stored in the correction image storage unit 87, two first offset images OP1 are used for the process of the determination unit 93 determining whether or not an offset image needs to be reacquired (that is, calibration needs to be reperformed).

Figure 14:
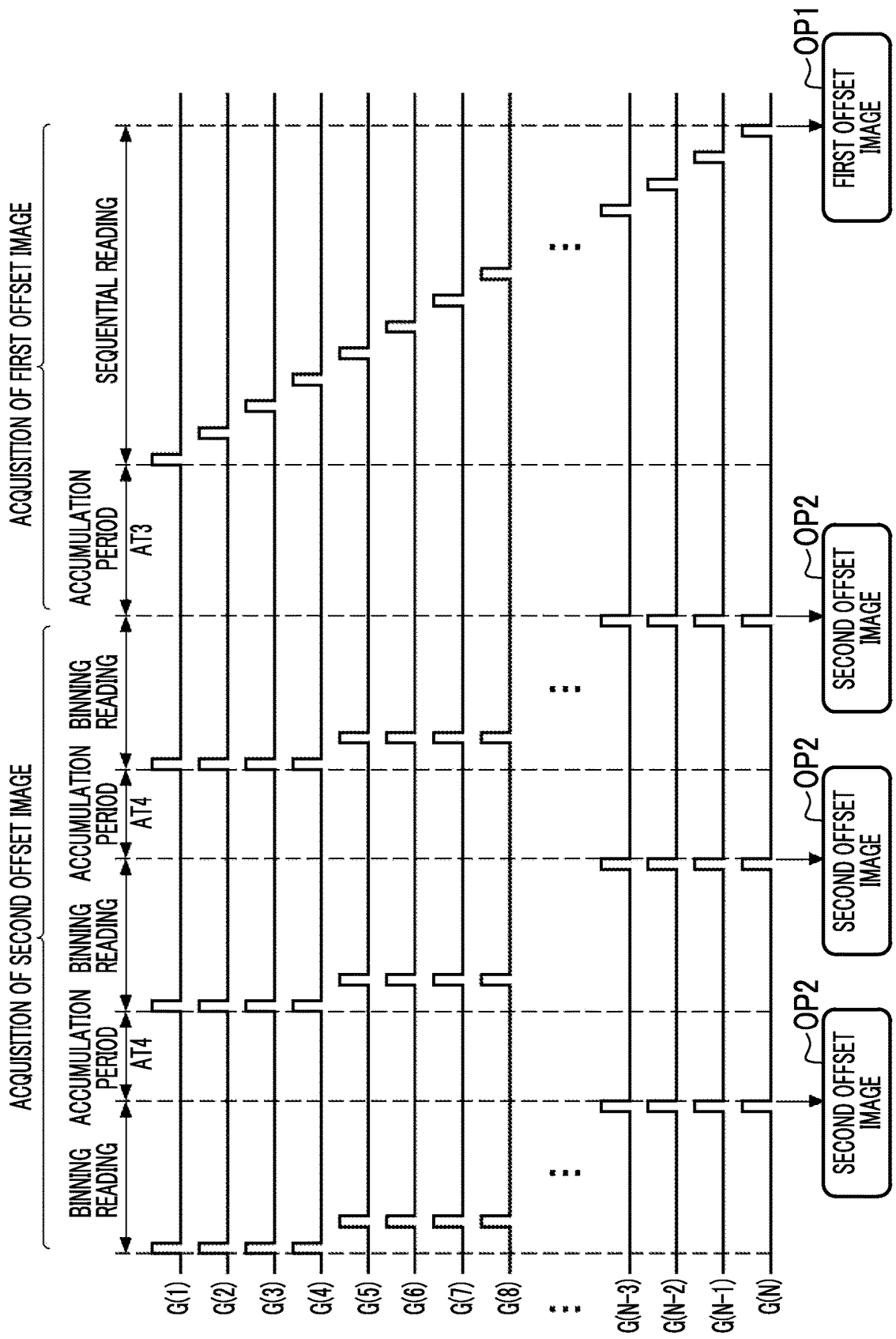
FIG. 14 is a timing chart illustrating the timing of the gate pulses in a case in which a second offset image is acquired.

As illustrated in FIG. 14, the second offset image acquisition unit 91 drives the reading unit 45 immediately before the first offset image acquisition unit 90 acquires each first offset image OP1 in a state in which no X-rays are emitted. The second offset image acquisition unit 91 performs the binning reading a plurality of times to acquire a plurality of second offset images OP2. The length of an accumulation period AT4 during the acquisition of each second offset image OP2 is the same. In addition, the operation of acquiring the second offset image OP2 also functions as a reset operation of discarding the charge accumulated in the pixel region 40 immediately before the first offset image OP1 is acquired.

The second offset image acquisition unit 91 may acquire at least one second offset image OP2 immediately before the first offset image OP1 is acquired.

The second offset image acquisition unit 91 stores the acquired one or more second offset images OP2 in the correction image storage unit 87 (see FIG. 12). The offset correction unit 84 uses the one or more second offset images OP2 stored in the correction image storage unit 87 for offset correction, which will be described in detail below. Further, the determination unit 93 uses one second offset image OP2 stored in the correction image storage unit 87 for the process of determining whether or not the offset image needs to be reacquired.

The reference image acquisition unit 92 performs a reference image acquisition process of acquiring a reference image RP by driving the reading unit 45 using the same reading method as the second offset image acquisition unit 91 in a state in which the gates (the gate electrodes of the TFTs 52) of all of the pixels 50 included in the pixel region 40 are turned off. That is, unlike the second offset image acquisition unit 91, the reference image acquisition unit 92 does not apply the gate pulses from the gate driver 41 to the scanning lines 53. Except this configuration, the reference image acquisition unit 92 drives the reading unit 45 using the same reading method as the second offset image acquisition unit 91.

The reference image acquisition unit 92 acquires one reference image RP. The reference image RP may be acquired before the first offset image OP1 and the second offset image OP2 are acquired or after the first offset image OP1 and the second offset image OP2 are acquired. Further, the reference image acquisition unit 92 may acquire the reference image RP for a period other than a calibration period.

The reference image acquisition unit 92 stores the acquired reference image RP in the correction image storage unit 87. The determination unit 93 uses the reference image RP stored in the correction image storage unit 87 for the process of determining whether or not the offset image needs to be reacquired.

Since the reference image RP is acquired in a state in which the gates of all of the pixels 50 are turned off, it does not include dark current noise (DCN) generated in the pixel 50 and mainly include fixed pattern noise (FPN).

The DCN is mainly caused by a dark current that is generated in each pixel 50 due to heat. The FPN is mainly caused by a variation in the characteristics of the integrator 60 connected to each signal line 54. Since the DCN is caused by heat, it varies due to a temperature change. In contrast, since the FPN is caused by the characteristics of the integrator 60, it is constant regardless of a temperature change.

In contrast, the first offset image OP1 and the second offset image OP2 include the DCN and the FPN. The immediately preceding offset image OPi acquired immediately before the X-ray imaging also includes the DCN and the FPN. The X-ray image XP acquired by the X-ray imaging includes the DCN and the FPN in addition to an X-ray component caused by irradiation with X-rays.

The determination unit 93 includes a first dark current distribution image acquisition unit 94, a second dark current distribution image acquisition unit 95, and a determination processing unit 96. The determination unit 93 operates in a case in which the validity of the offset images (the first offset image OP1 and the second offset image OP2) acquired by the calibration as correction data is evaluated to determine whether or not reacquisition is needed.

Since a plurality of first offset images OP1 are acquired by one operation, the processing time of the calibration process is long (for example, several tens of seconds). Therefore, in some cases, temperature irregularity occurs in the pixel region 40 due to a temperature change during the calibration. In a case in which the temperature irregularity occurs, the distribution of the DCN (hereinafter, referred to as a dark current distribution) included in the first offset image OP1 and the second offset image OP2 changes.

The first dark current distribution image acquisition unit 94 performs a first dark current distribution image acquisition process of calculating a difference between two first offset images OP1 having different accumulation times to acquire a first dark current distribution image DP1. The first dark current distribution image acquisition unit 94 stores the acquired first dark current distribution image DP1 in the correction image storage unit 87.

The second dark current distribution image acquisition unit 95 performs a second dark current distribution image acquisition process of calculating a difference between the second offset image OP2 and the reference image RP to acquire a second dark current distribution image DP2. The second dark current distribution image acquisition unit 95 stores the acquired second dark current distribution image DP2 in the correction image storage unit 87.

The determination processing unit 96 performs a determination process of determining whether or not the first offset image OP1 and the second offset image OP2 need to be reacquired on the basis of a correction error of a corrected image obtained by correcting the first dark current distribution image DP1 on the basis of the second dark current distribution image DP2.

Figure 15:
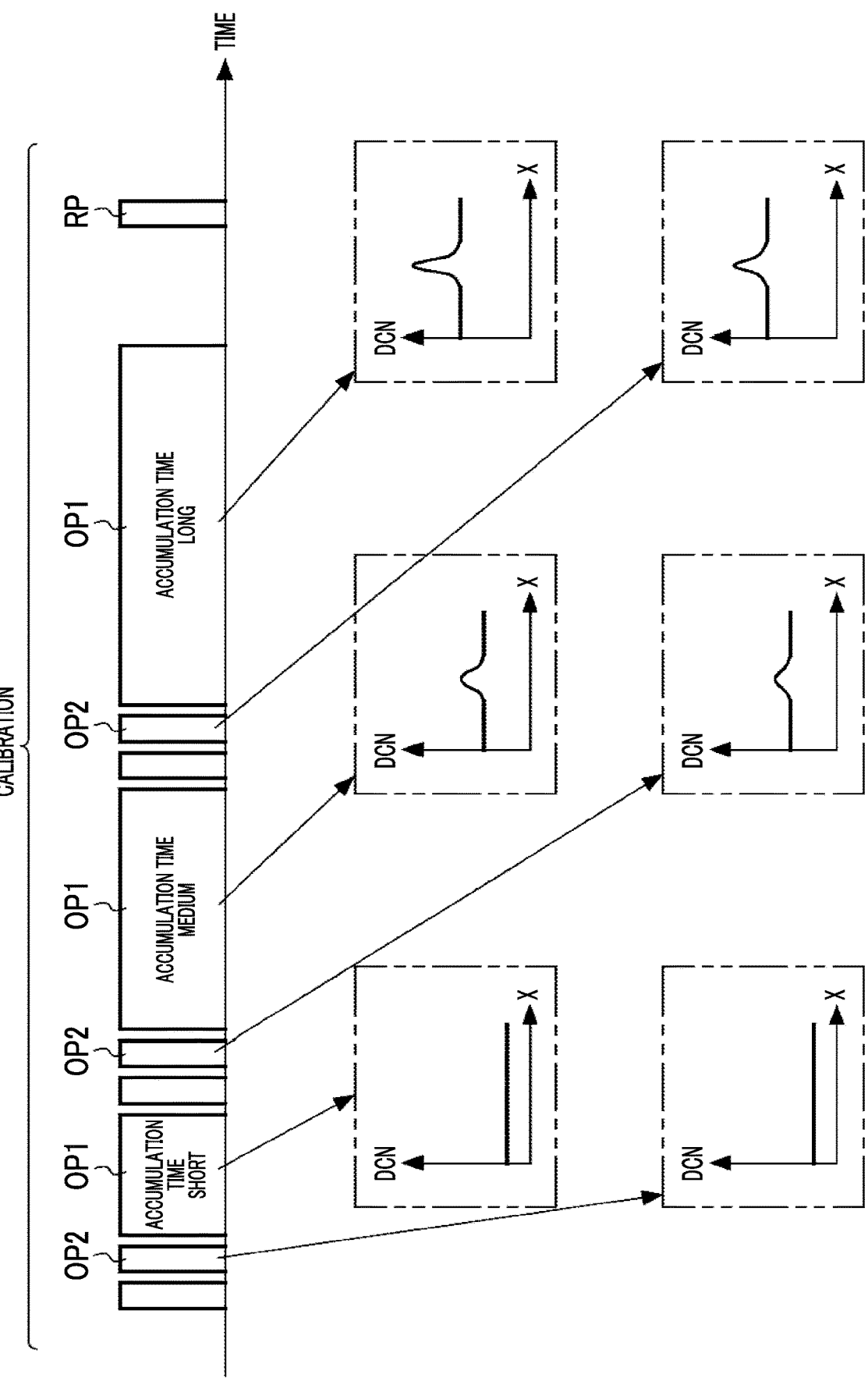
FIG. 15 is a diagram illustrating an example of a change in a dark current distribution that occurs during calibration.

During the calibration, the length of the accumulation period AT3 (accumulation time) is changed to a plurality of different values (see FIG. 13). For example, as illustrated in FIG. 15, during the calibration, three first offset images OP1 having accumulation times of "short", "medium", and "long" are acquired. Further, for example, immediately before the acquisition of each first offset image OP1, two second offset images OP2 are acquired. Then, for example, the reference image RP is independently acquired after the first offset image OP1 and the second offset image OP2 are acquired.

FIG. 15 schematically illustrates an example in which the dark current distribution varies due to a temperature change occurring during the calibration. Each graph in FIG. 15 shows the dependency of the DCN in the X direction (see FIG. 4). The temperature change during the calibration occurs due to, for example, the influence of heat generated in, for example, an electric substrate in the electronic cassette 13.

In a case in which the temperature in the pixel region 40 is uniform, the amount of DCN from each pixel 50 is substantially the same. Therefore, the dark current distribution is substantially uniform. Immediately after the start of the calibration, the amount of heat generated from, for example, the electric substrate is small. Therefore, the temperature distribution is uniform, and the dark current distribution is substantially uniform. Therefore, in the example illustrated in FIG. 15, the dark current distributions of the first offset image OP1 having the accumulation time of "short" and the second offset image OP2 which are acquired immediately after the start of the calibration are substantially uniform.

In a case in which there is no temperature change during the calibration and the temperature is uniform, the amount of DCN is basically proportional to the accumulation time. However, in a case in which a temperature change occurs during the calibration, the amount of DCN is not proportional to the accumulation time. Further, in a case in which local heat is generated in, for example, the electric substrate during the calibration, a portion of the dark current distribution locally changes. As a result, the dark current distribution is not uniform. In the example illustrated in FIG. 15, in a case in which the accumulation time is "medium" and "long", the dark current distributions of the first offset image OP1 and the second offset image OP2 vary locally.

In a case in which a set of the first offset image OP1 and the second offset image OP2 having a similar dark current distribution shape is used for the correction process of the offset correction unit 84, the dark current distributions of the first offset image OP1 and the second offset image OP2 cancel each other. Therefore, even in a case in which the dark current distribution varies, no problems occur. However, in a case in which the set of the first offset image OP1 and the second offset image OP2 that do not have a similar dark current distribution shape is used for the correction process of the offset correction unit 84, the dark current distributions of the first offset image OP1 and the second offset image OP2 do not cancel each other, and the correction error remains.

The determination processing unit 96 determines in advance whether or not the correction error is less than an allowable value even in a case in which the first offset image OP1 and the second offset image OP2 acquired by the calibration are used for the correction process of the offset correction unit 84. That is, the determination processing unit 96 determines the validity of using the first offset image OP1 and the second offset image OP2 acquired by the calibration for the correction of the X-ray image XP.

Figure 16:
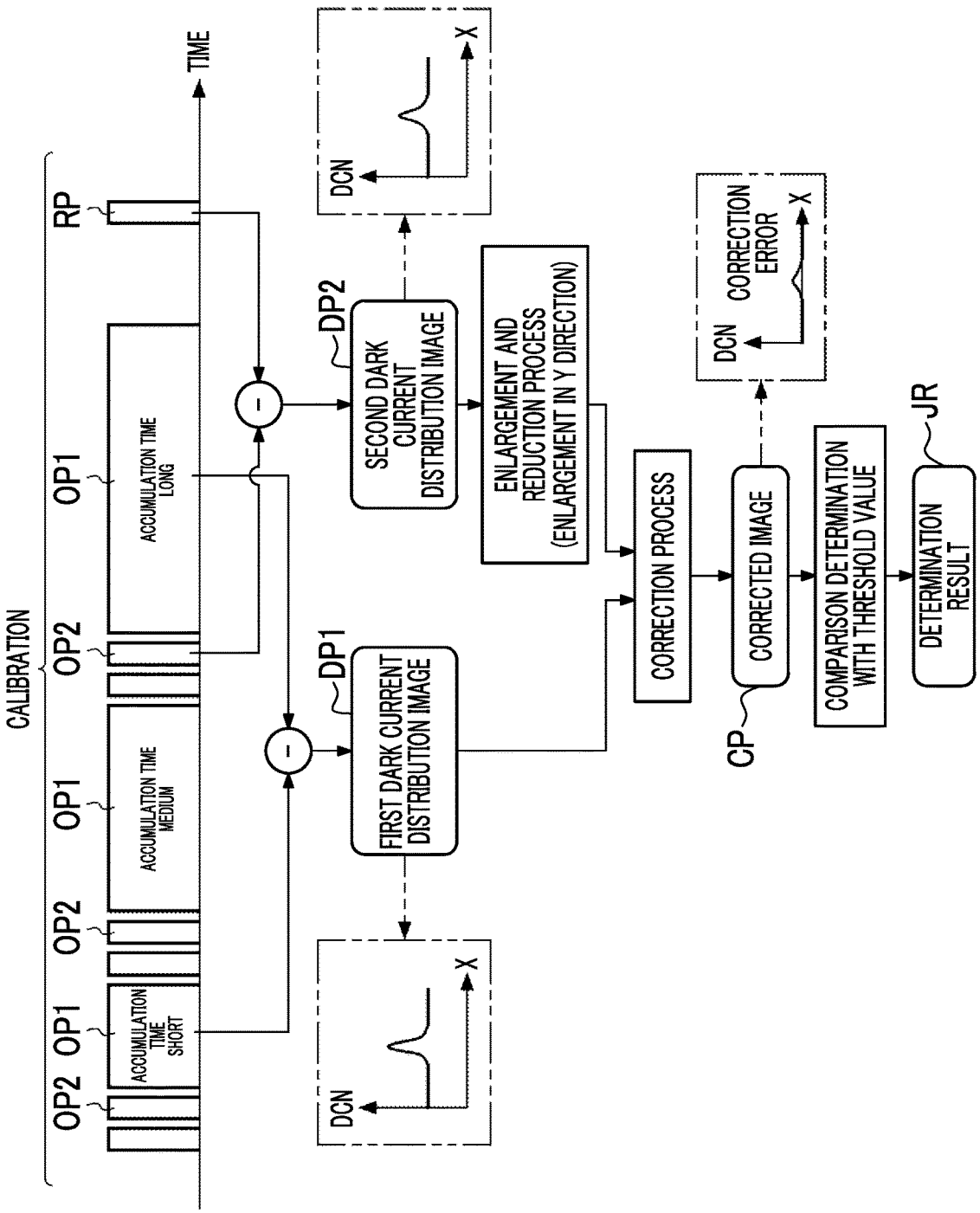
FIG. 16 is a diagram illustrating a specific determination process.

FIG. 16 illustrates a specific determination process performed by the determination unit 93. As illustrated in FIG. 16, for example, the first dark current distribution image acquisition unit 94 subtracts the first offset image OP1 having the accumulation time of "short" from the first offset image OP1 having the accumulation time of "long" to acquire the first dark current distribution image DP1. Since the FPN does not depend on the temperature, it is constant regardless of the difference in the accumulation time. Therefore, since the FPN included in the two first offset images OP1 is canceled by the subtraction process, the first dark current distribution image DP1 includes almost only the DCN component.

For example, the second dark current distribution image acquisition unit 95 subtracts the reference image RP from the second offset image OP2 acquired immediately before the first offset image OP1 having the accumulation time of "long" to acquire the second dark current distribution image DP2. Since the reference image RP does not include the DCN and mainly includes only the FPN, the second dark current distribution image DP2 includes almost only the DCN component.

First, the determination processing unit 96 performs an enlargement and reduction process on the second dark current distribution image DP2. Specifically, since the second dark current distribution image DP2 is a difference image between the reference image RP and the second offset image OP2 acquired by the binning reading in the Y direction (see FIG. 9), an enlargement process is performed on the second dark current distribution image DP2 in the Y direction (in this example, the second dark current distribution image DP2 is enlarged four times). Therefore, the image sizes of the first dark current distribution image DP1 and the second dark current distribution image DP2 are equal to each other. The enlargement process is performed, for example, by a complement process.

The determination processing unit 96 may perform an accumulation time multiplication process on the second dark current distribution image DP2 in order to match the substantial accumulation times of the first dark current distribution image DP1 and the second dark current distribution image DP2. The substantial accumulation time of the first dark current distribution image DP1 is the difference between the accumulation times of the two first offset images OP1 used to generate the first dark current distribution image DP1. The accumulation time of the second dark current distribution image DP2 is the accumulation time of the second offset image OP2.

The determination processing unit 96 performs a correction process of correcting the first dark current distribution image DP1 on the basis of the second dark current distribution image DP2 subjected to the enlargement and reduction process to generate a corrected image CP. For example, the determination processing unit 96 subtracts an image obtained by multiplying the second dark current distribution image DP2 subjected to the enlargement and reduction process by a correction coefficient from the first dark current distribution image DP1 to generate the corrected image CP. In the correction, the determination processing unit 96 appropriately changes the correction coefficient to perform the correction such that the correction error is minimized.

In a case in which the dark current distribution of the first dark current distribution image DP1 and the dark current distribution of the second dark current distribution image DP2 have a similar shape, the correction error is almost zero. In a case in which the dark current distribution of the first dark current distribution image DP1 and the dark current distribution of the second dark current distribution image DP2 do not have a similar shape, but have different shapes, a correction error corresponding to the difference in shape remains in the corrected image CP.

The determination processing unit 96 compares the correction error included in the corrected image CP with a threshold value to determine whether or not the first offset image OP1 and the second offset image OP2 need to be reacquired. The determination processing unit 96 determines that the reacquisition is needed in a case in which the correction error is equal to or greater than the threshold value. For example, the determination processing unit 96 compares an average value of the correction error with a threshold value and determines that the reacquisition is needed in a case in which the average value is equal to or greater than the threshold value.

The determination processing unit 96 outputs a determination result JR. The determination result JR output from the determination processing unit 96 is transmitted to the console 14 through, for example, the communication I/F 44. In the console 14, the determination result JR is displayed on the display 14B. The operator can operate the input device 14A on the basis of the determination result JR displayed on the display 14B to instruct the reperformance of the calibration. In addition, the calibration processing unit 83 may be configured to automatically reperform the calibration process according to the determination result JR output from the determination processing unit 96.

In a case in which the correction error is less than the threshold value, it is presumed that one first offset image OP1 selected from the plurality of first offset images OP1 acquired by the calibration and the second offset image OP2 acquired immediately before the first offset image OP1 have a substantially similar dark current distribution shape.

Figure 17:
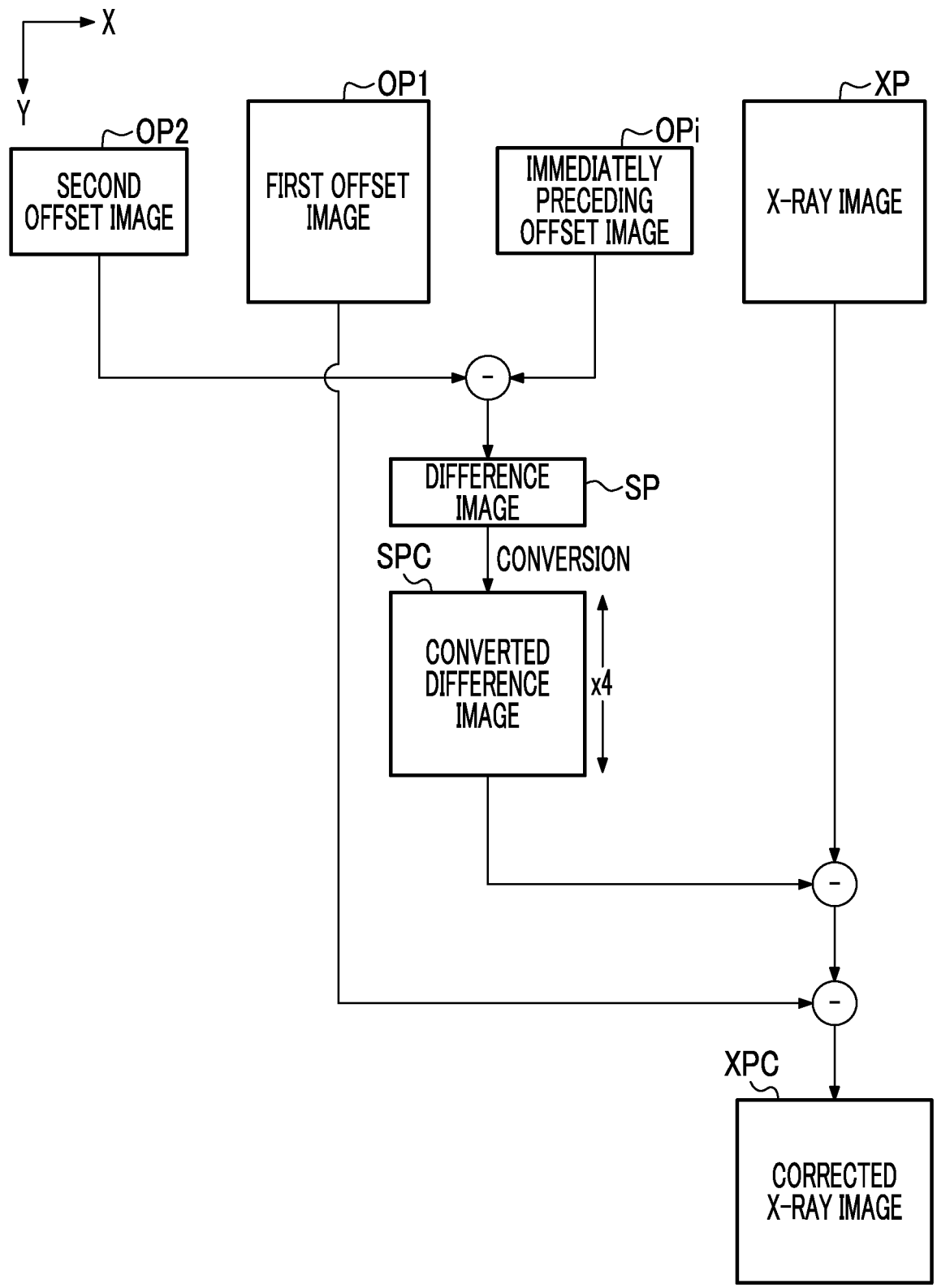
FIG. 17 is a diagram illustrating a correction process.

FIG. 17 illustrates the outline of offset correction by the offset correction unit 84. The offset correction unit 84 performs a correction process of correcting the X-ray image XP on the basis of the first offset image OP1, the second offset image OP2, and the immediately preceding offset image OPi. In a case in which the dark current distributions of the first offset image OP1 and the second offset image OP2 have a substantially similar shape, it is possible to perform offset correction on the X-ray image XP with high accuracy.

Figure 18:
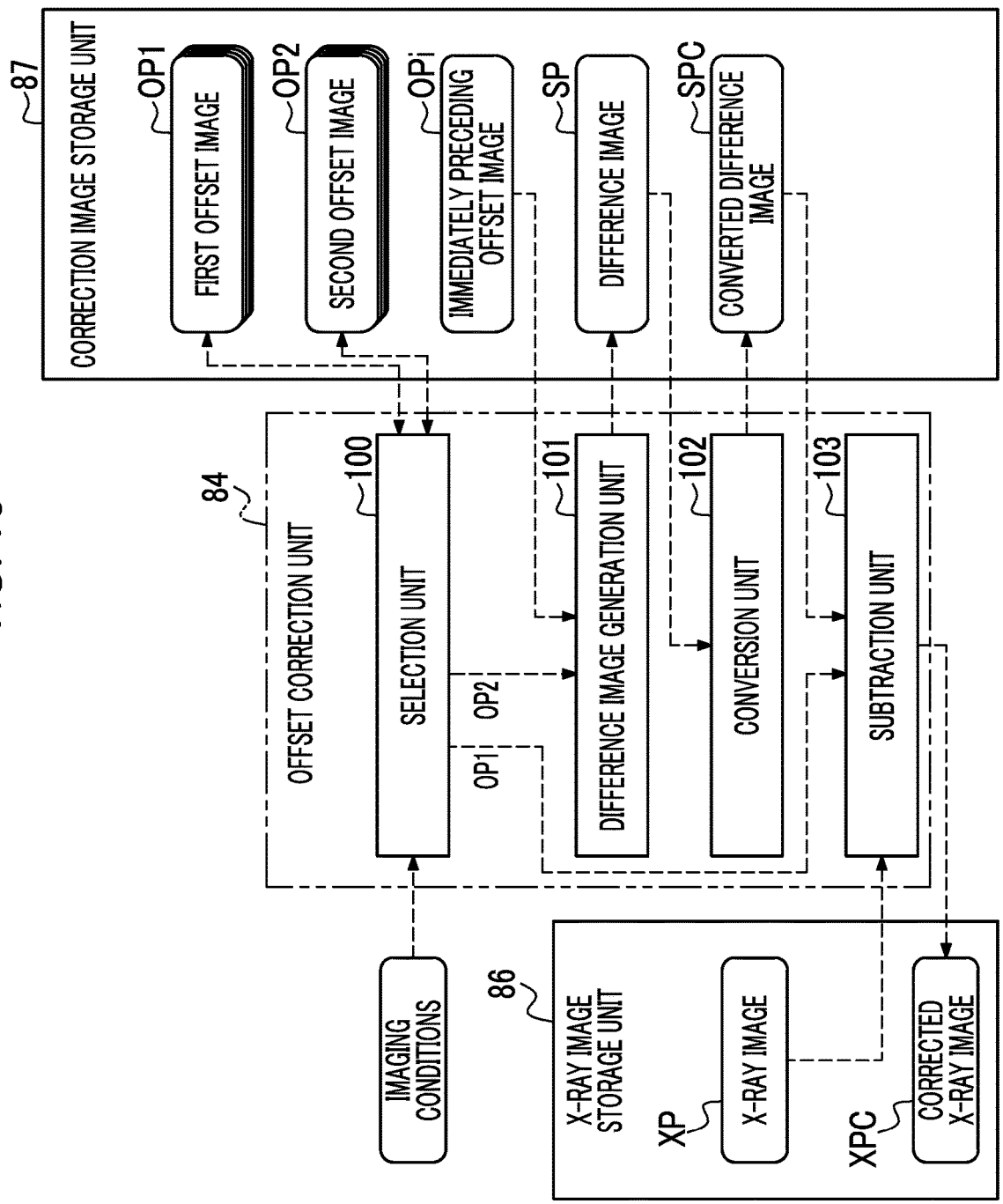
FIG. 18 is a block diagram illustrating a functional configuration of an offset correction unit.

As illustrated in FIG. 18, the offset correction unit 84 includes a selection unit 100, a difference image generation unit 101, a conversion unit 102, and a subtraction unit 103. The selection unit 100 performs a selection process of selecting the first offset image OP1 acquired at the accumulation time corresponding to the X-ray irradiation time included in the imaging conditions from a plurality of first offset images OP1 acquired during the calibration on the basis of the imaging conditions of the X-ray imaging. In addition, the selection unit 100 selects the second offset image OP2 acquired immediately before the selected first offset image OP1 from a plurality of second offset images OP2.

The selection unit 100 supplies the selected first offset image OP1 to the subtraction unit 103. Further, the selection unit 100 supplies the selected second offset image OP2 to the difference image generation unit 101.

The difference image generation unit 101 performs a difference image generation process of acquiring the second offset image OP2 from the selection unit 100, acquiring the immediately preceding offset image OPi from the correction image storage unit 87, and generating a difference image SP between the acquired second offset image OP2 and the acquired immediately preceding offset image OPi. Since the immediately preceding offset image OPi most immediately before the X-ray imaging is affected by irradiation with X-rays, the difference image generation unit 101 selects an immediately preceding offset image OPi other than the immediately preceding image most immediately before the X-ray imaging. For example, the difference image generation unit 101 subtracts the second offset image OP2 from the immediately preceding offset image OPi for each corresponding addition pixel to generate the difference image SP. The difference image generation unit 101 stores the generated difference image SP in the correction image storage unit 87.

The conversion unit 102 acquires the difference image SP from the correction image storage unit 87 and performs, on the acquired difference image SP, at least one of the accumulation time multiplication process or the enlargement and reduction process for adjusting an image size to the X-ray image XP. In this embodiment, both the multiplication process and the enlargement and reduction process are performed on the difference image SP.

The conversion unit 102 performs a multiplication process of multiplying each pixel value of the difference image SP by the ratio (AT1/AT2) of the accumulation period AT1 in the X-ray imaging to the accumulation period AT2 in the acquisition of the immediately preceding offset image OPi as a coefficient. In addition, the conversion unit 102 performs an enlargement process of enlarging the difference image SP in the direction (the Y direction in this embodiment) in which the image has been reduced by the binning reading to adjust the image size of the difference image SP to the image size of the X-ray image XP (see FIG. 17). This enlargement process is performed, for example, by a complement process.

In addition, the conversion unit 102 multiplies a conversion coefficient corresponding to the difference between the reading method (sequential reading method) in the X-ray imaging and the reading method (binning reading method) in the acquisition of the immediately preceding offset image OPi. In the sequential reading method, the charge corresponding to one pixel is converted into a pixel signal by the signal processing circuit 42. In contrast, in the binning reading method, the charge output from a plurality of pixels is added and is converted into a pixel signal by the signal processing circuit 42. The conversion characteristics of the signal processing circuit 42 converting the charge into the pixel signal are not necessarily linear. For example, the added pixel signal based on the charge corresponding to four pixels is likely to deviate from a value that is four times as large as the pixel signal based on the charge corresponding to one pixel. Therefore, the conversion unit 102 multiplies each pixel value of the difference image SP by a conversion coefficient for correcting the nonlinearity of the conversion characteristics of the signal processing circuit 42. The conversion unit 102 stores a converted difference image SPC obtained by converting the difference image SP in the correction image storage unit 87.

The subtraction unit 103 acquires the X-ray image XP from the X-ray image storage unit 86, acquires the converted difference image SPC from the correction image storage unit 87, and acquires the first offset image OP1 from the selection unit 100. The subtraction unit 103 performs a subtraction process of subtracting each of the converted difference image SPC and the first offset image OP1 from the acquired X-ray image XP. The subtraction unit 103 stores a corrected X-ray image XPC obtained as a result of the subtraction process in the X-ray image storage unit 86. For example, the corrected X-ray image XPC is displayed on the display 14B (see FIG. 1).

Figure 19:
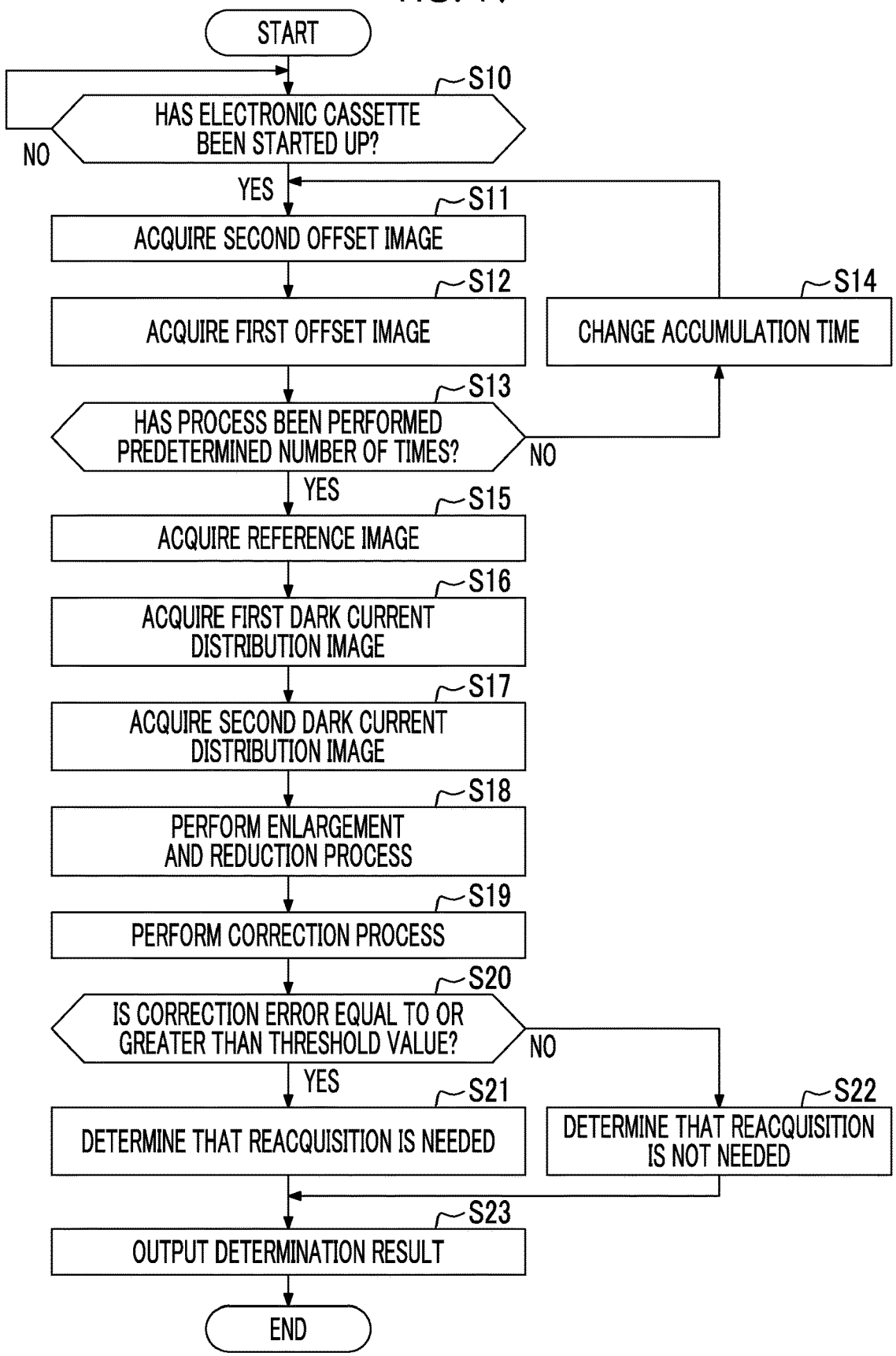
FIG. 19 is a flowchart illustrating a processing procedure during calibration.
Figure 20:
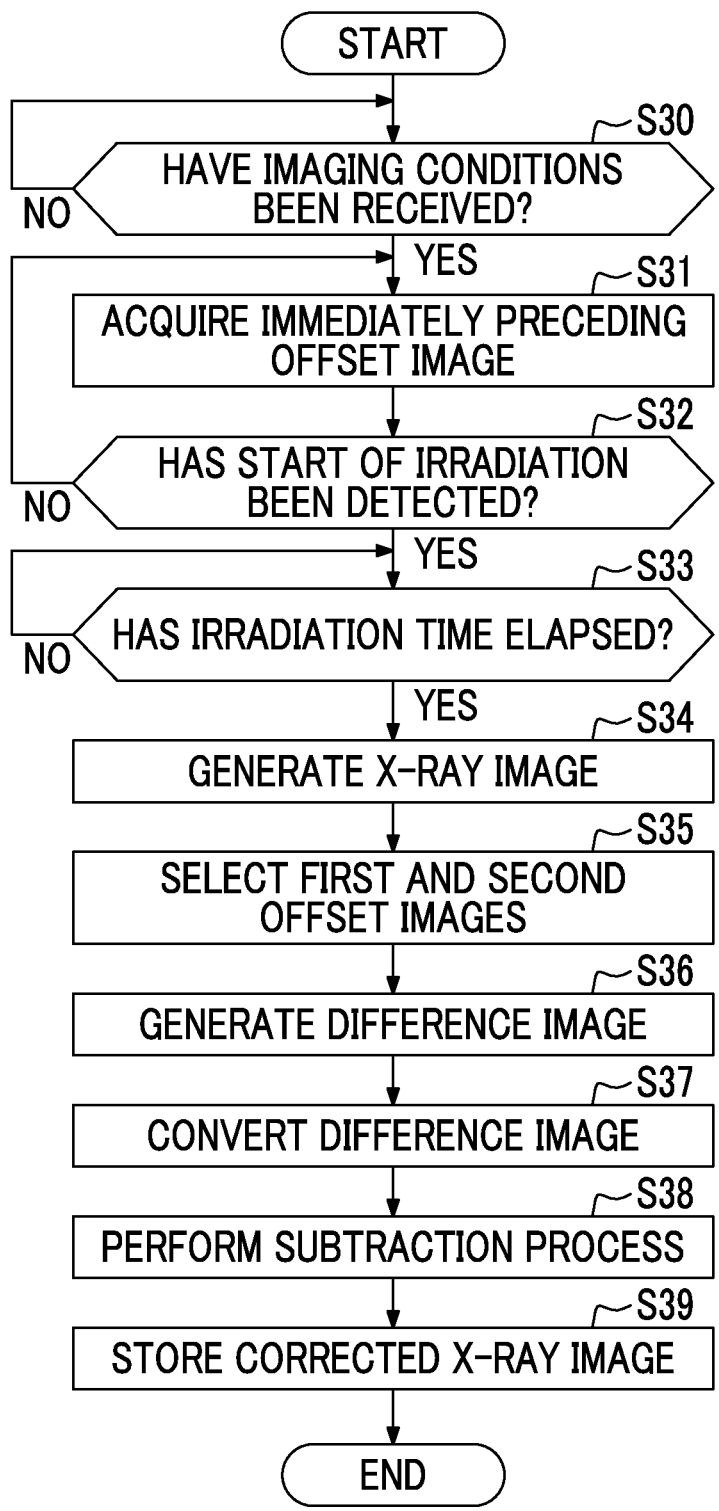
FIG. 20 is a flowchart illustrating a processing procedure during X-ray imaging.

Next, the operation of the X-ray imaging system 2 having the above-mentioned configuration will be described with reference to flowcharts illustrated in FIGS. 19 and 20. FIG. 19 is a flowchart illustrating a processing procedure during the calibration. FIG. 20 is a flowchart illustrating a processing procedure during the X-ray imaging.

First, the control unit 43 of the electronic cassette 13 determines whether or not the electronic cassette 13 has been started up by the pressure of the power switch 33 (see FIG. 3) of the electronic cassette 13 by the operator (Step S10).

In a case in which the control unit 43 determines that the electronic cassette 13 has been started up (Step S10: YES), the second offset image acquisition unit 91 drives the reading unit 45 using the binning reading method to acquire the second off image OP2 (Step S11). Then, the first offset image acquisition unit 90 drives the reading unit 45 using the sequential reading method to acquire the first offset image OP1 (Step S12).

Next, the control unit 43 determines whether or not Step S11 and Step S12 have been performed a predetermined number of times (for example, three times) (Step S13). In a case in which Step S11 and Step S12 have not been performed the predetermined number of times (Step S13: NO), the control unit 43 changes the accumulation time during the acquisition of the first offset image OP1 in Step S12 (Step S14). Then, the control unit 43 returns the process to Step S11.

In a case in which Step S11 and Step S12 have been performed the predetermined number of times (Step S13: YES), the control unit 43 moves the process to Step S15. For example, three first offset images OP1 having the accumulation times of "short", "medium", and "long" and one or more second offset images OP2 acquired immediately before each first offset image OP1 are stored in the correction image storage unit 87 by Step S11 and Step S12.

In Step S15, the reference image acquisition unit 92 acquires the reference image RP by driving the reading unit 45 using the binning reading method in a state in which the gates of all of the pixels 50 are turned off. The reference image RP is stored in the correction image storage unit 87.

Next, the first dark current distribution image acquisition unit 94 calculates the difference between two first offset images OP1 having different accumulation times to acquire the first dark current distribution image DP1 (Step S16). For example, the first dark current distribution image acquisition unit 94 subtracts the first offset image OP1 having the accumulation time of "short" from the first offset image OP1 having the accumulation time of "long" to acquire the first dark current distribution image DP1.

Then, the second dark current distribution image acquisition unit 95 calculates the difference between the second offset image OP2 and the reference image RP to acquire the second dark current distribution image DP2 (Step S17). For example, the second dark current distribution image acquisition unit 95 subtracts the reference image RP from the second offset image OP2 acquired immediately before the first offset image OP1 having the accumulation time of "long" to acquire the second dark current distribution image DP2.

Then, the determination processing unit 96 performs the enlargement and reduction process on the second dark current distribution image DP2. The determination processing unit 96 performs, for example, an enlargement process of enlarging the second dark current distribution image DP2 in the Y direction (Step S18). In addition, the determination processing unit 96 may perform the accumulation time multiplication process on the second dark current distribution image DP2 in addition to the enlargement and reduction process.

Next, the determination processing unit 96 performs a correction process of correcting the first dark current distribution image DP1 on the basis of the second dark current distribution image DP2 subjected to the enlargement and reduction process to generate the corrected image CP (Step S19). Then, the determination processing unit 96 compares the correction error included in the corrected image CP with the threshold value and determines whether or not the correction error is equal to or greater than the threshold value (Step S20).

In a case in which the correction error is equal to or greater than the threshold value (Step S20: YES), the determination processing unit 96 determines that the first offset image OP1 and the second offset image OP2 need to be reacquired (Step S21). On the other hand, in a case in which the correction error is less than the threshold value (Step S20: NO), the determination processing unit 96 determines that the first offset image OP1 and the second offset image OP2 do not need to be reacquired (Step S22). Then, the determination processing unit 96 outputs the determination result JR in Step S21 or Step S22 (Step S23).

In this way, the calibration process ends. The control unit 43 reperforms the calibration process in a case in which the first offset image OP1 and the second offset image OP2 need to be reacquired on the basis of the determination result JR. The first offset image OP1 and the second offset image OP2 stored in the correction image storage unit 87 are updated by this process. The control unit 43 may reperform the calibration process in response to an instruction from the operator. In addition, the reference image RP may not be acquired in a case in which the calibration process is reperformed. The reason is that, since the reference image RP has low temperature dependence, the necessity to update the reference image RP is low.

After the calibration ends, in the X-ray imaging, the operator sets the subject at the imaging position of the upright imaging stand 15 or the decubitus imaging stand 16 and adjusts the position of the electronic cassette 13. In addition, the operator adjusts the position of the X-ray source 10 and the size of the irradiation field according to the position of the electronic cassette 13 and the size of an imaging part of the subject. Then, the operator sets imaging conditions in the radiation source control device 11 and the console 14. The imaging conditions set in the console 14 are transmitted to the electronic cassette 13.

The control unit 43 of the electronic cassette 13 waits for the imaging conditions transmitted from the console 14 (Step S30). In a case in which the control unit 43 receives the imaging conditions from the console 14 through the communication I/F 44 (Step S30: YES), the immediately preceding offset image acquisition unit 81 drives the reading unit 45 using the binning reading method to acquire the immediately preceding offset image OPi (Step S31).

The irradiation start detection unit 82 operates during the binning reading operation to detect the start of irradiation with X-rays on the basis of the added pixel signal AS obtained during the binning reading (Step S32). In a case in which the irradiation start detection unit 82 does not detect the start of irradiation with X-rays (Step S32: NO), the process of acquiring the immediately preceding offset image OPi in Step S31 is repeated.

In the X-ray imaging, the operator presses the irradiation switch 12 halfway to instruct preparation for imaging. In a case in which the irradiation switch 12 is pressed halfway, a warm-up instruction signal is issued to the high voltage generator 21, and the warm-up of the X-ray source 10 is started. Then, in a case in which the operator fully presses the irradiation switch 12, X-rays are emitted from the X-ray source 10 to the subject.

In a case in which the irradiation start detection unit 82 detects the start of irradiation with X-rays (Step S32: YES), the X-ray image generation unit 80 stops the binning reading and starts measuring the irradiation time using the timer 73. Then, the pixel region 40 is changed to a charge accumulation state and accumulates charge corresponding to the amount of X-rays emitted through the subject. The X-ray image generation unit 80 determines whether or not the irradiation time included in the imaging conditions has elapsed (Step S33).

In a case in which the X-ray image generation unit 80 determines that the irradiation time has elapsed (Step S33: YES), it drives the reading unit 45 using the sequential reading method to generate the X-ray image XP (Step S34).

Then, the selection unit 100 selects the first offset image OP1 acquired at the accumulation time corresponding to the X-ray irradiation time included in the imaging conditions on the basis of the imaging conditions received in Step S30 (Step S35). Further, in this case, the selection unit 100 selects the second offset image OP2 acquired immediately before the selected first offset image OP1 from a plurality of second offset images OP2.

Then, the difference image generation unit 101 generates the difference image SP between the second offset image OP2 selected by the selection unit 100 and the immediately preceding offset image OPi (Step S36). Then, the conversion unit 102 performs the accumulation time multiplication process, the enlargement and reduction process for adjusting the image size to the X-ray image XP, and the process of multiplying a conversion coefficient corresponding to the difference between the reading methods on the difference image SP to generate the converted difference image SPC (Step S37).

Then, the subtraction unit 103 performs the subtraction process of subtracting each of the converted difference image SPC and the first offset image OP1 selected by the selection unit 100 from the X-ray image XP to generate the corrected X-ray image XPC (Step S38). The subtraction unit 103 stores the generated corrected X-ray image XPC in the X-ray image storage unit 86 (Step S39).

Figure 21:
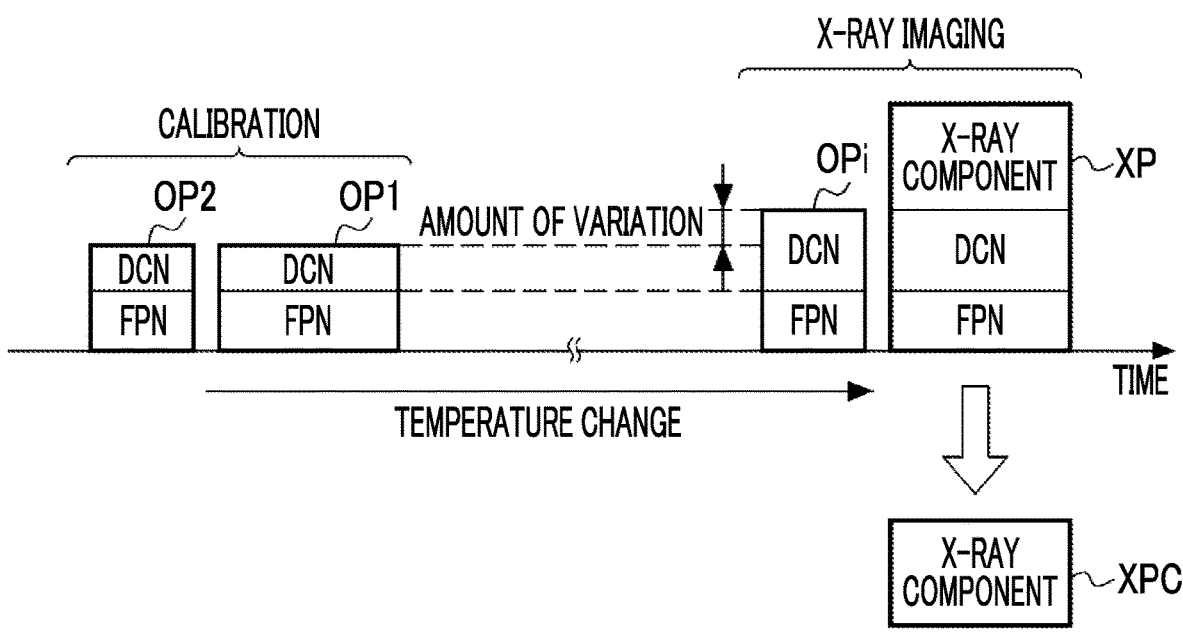
FIG. 21 is a schematic diagram illustrating noise components included in an X-ray image, an immediately preceding offset image, the first offset image, and the second offset image.

FIG. 21 is a schematic diagram illustrating noise components included in the X-ray image XP, the immediately preceding offset image OPi, the first offset image OP1, and the second offset image OP2. Since the immediately preceding offset image OPi, the first offset image OP1, and the second offset image OP2 are obtained in a state in which no X-rays are emitted, the X-ray image XP mainly including the DCN and the FPN includes the DCN and the FPN in addition to the X-ray components caused by irradiation with X-rays.

The calibration is performed, for example, in a case in which the electronic cassette 13 is started up. Therefore, in some cases, it takes a long time from the calibration to the X-ray imaging. In a case in which the temperature changes during the period, the DCN changes. In particular, since the electronic cassette 13 is portable and small in size, it has a small heat capacity. Therefore, the electronic cassette 13 is likely to be affected by an environmental temperature change. Further, since the electronic cassette 13 periodically detects the start of irradiation, it consumes a large amount of power and generates heat. Therefore, a temperature change is likely to occur. As such, in the electronic cassette 13, the amount of variation in DCN is large. Therefore, it is difficult to perform offset correction on the X-ray image XP with high accuracy, using only the offset image acquired in the calibration.

In the electronic cassette 13 according to this embodiment, the X-ray image XP is corrected on the basis of the immediately preceding offset image OPi acquired in a state in which no X-rays are emitted immediately before the X-ray imaging including the X-ray image generation process. Therefore, it is possible to perform offset correction on the X-ray image XP with high accuracy.

Further, in the electronic cassette 13 according to this embodiment, the X-ray image XP is corrected on the basis of the first offset image OP1 and the difference image SP between the second offset image OP2 and the immediately preceding offset image OPi. Since the first offset image OP1 is an offset image acquired by the same reading method as the X-ray image XP, the accuracy of offset correction is further improved.

In addition, in the electronic cassette 13 according to this embodiment, the second offset image OP2 is acquired immediately before the first offset image OP1 is acquired. With this configuration, the first offset image OP1 and the second offset image OP2 are acquired at the same reading timing as the X-ray image XP acquired in the X-ray imaging and the immediately preceding offset image OPi. Therefore, the accuracy of offset correction is further improved.

Further, in the electronic cassette 13 according to this embodiment, the pixel signal is read from the pixel region 40 a plurality of times by the binning reading to acquire the immediately preceding offset images OPi in a state in which no X-rays are emitted immediately before the X-ray imaging. Therefore, it is possible to shorten a time lag immediately before the X-ray imaging.

The difference between the dark current distributions of the first offset image OP1 and the second offset image OP2 needs to be less than an allowable value in order to perform the above-mentioned offset correction with high accuracy. In a case in which the difference between the dark current distributions of the first offset image OP1 and the second offset image OP2 is equal to or greater than the allowable value, it is desirable to reacquire the first offset image OP1 and the second offset image OP2.

In the electronic cassette 13 according to this embodiment, the difference between two first offset images OP1 having different accumulation times is calculated to acquire the first dark current distribution image DP1 indicating the dark current distribution of the first offset image OP1. In addition, in the electronic cassette 13 according to this embodiment, the difference between the second offset image OP2 and the reference image RP is calculated to acquire the second offset image OP2 indicating the dark current distribution of the second offset image OP2. The correction error of the corrected image CP obtained by correcting the first dark current distribution image DP1 on the basis of the second dark current distribution image DP2 can be evaluated to determine whether or not the first offset image OP1 and the second offset image OP2 need to be reacquired.

In the above-described embodiment, one first offset image OP1 is acquired for each accumulation time during calibration. However, instead of this configuration, a plurality of first offset images OP1 may be acquired for each accumulation time. In this case, the plurality of first offset images OP1 obtained for each accumulation time may be averaged to generate an average image, and the generated average image may be used to acquire the first dark current distribution image DP1. Similarly, the second dark current distribution image DP2 may be acquired using an average image obtained by averaging a plurality of second offset images OP2. As such, in a case in which a plurality of first offset images OP1 and second offset images OP2 are acquired, the calibration time further increases, and there is a high possibility that a temperature change will occur. Therefore, the reacquisition determination process according to the technology of the present disclosure is useful.

Further, in the above-described embodiment, the offset correction is performed using one immediately preceding offset image OPi acquired immediately before the X-ray imaging. However, the offset correction may be performed using an average image obtained by averaging a plurality of immediately preceding offset images OPi acquired immediately before the X-ray imaging. In this case, since the immediately preceding offset image OPi most immediately before the X-ray imaging is affected by irradiation with X-rays, it is preferably excluded from the averaging target for generating the average image.

Further, in the above-described embodiment, the first dark current distribution image acquisition unit 94 acquires the first dark current distribution image DP1 on the basis of the first offset image OP1 having the longest accumulation time and the first offset image OP1 having the shortest accumulation time among a plurality of first offset images OP1 acquired during the calibration. However, the technology of the present disclosure is not limited thereto. The first dark current distribution image acquisition unit 94 may acquire the first dark current distribution image DP1 on the basis of two first offset images OP1 having different accumulation times among the plurality of first offset images OP1.

Further, in the above-described embodiment, the second dark current distribution image acquisition unit 95 acquires the second dark current distribution image DP2 on the basis of the reference image RP and the second offset image OP2 acquired immediately before the first offset image OP1 having the longest accumulation time among a plurality of second offset images OP2 acquired during the calibration. However, the technology of the present disclosure is not limited thereto. The second dark current distribution image acquisition unit 95 may acquire the second dark current distribution image DP2 on the basis of the reference image RP and the second offset image OP2 acquired immediately before the first offset image OP1 other than the first offset image OP1 having the longest accumulation time.

In the above-described embodiment, the reading unit 45 is driven by the binning reading method to acquire the immediately preceding offset image OPi and the second offset image OP2. However, the reading unit 45 may be driven by the sequential reading method to acquire the immediately preceding offset image OPi and the second offset image OP2. In this case, the accumulation time during the acquisition of the immediately preceding offset image OPi and the second offset image OP2 may be shorter than the accumulation time during the acquisition of the X-ray image XP and the first offset image OP1. That is, the immediately preceding offset image OPi and the second offset image OP2 may be acquired in a shorter accumulation time than the X-ray image XP or by the binning reading.

Further, in the above-described embodiment, only the offset correction is performed as the correction process. However, in addition to the offset correction, for example, the following processes may be performed: gain correction for correcting a variation in the sensitivity of the image detection unit 30 to irradiation with X-rays; and defective pixel correction.

Further, the technology of the present disclosure is not limited to X-rays and can be applied to a system that captures the image of the subject using other kinds of radiation such as γ-rays.

In the above-described embodiment, for example, the following various processors can be used as a hardware structure of processing units performing various processes, such as the X-ray image generation unit 80, the immediately preceding offset image acquisition unit 81, the irradiation start detection unit 82, the calibration processing unit 83, and the offset correction unit 84.

The various processors include, for example, a CPU, a programmable logic device (PLD), a dedicated electric circuit. As is well known, the CPU is a general-purpose processor that executes software (program) to function as various processing units. The PLD is a processor whose circuit configuration can be changed after manufacture, such as a field programmable gate array (FPGA). The dedicated electric circuit is a processor that has a dedicated circuit configuration designed to perform a specific process, such as an application specific integrated circuit (ASIC).

One processing unit may be configured by one of the various processors or a combination of two or more processors of the same type or different types (for example, a combination of a plurality of FPGAs and a combination of a CPU and an FPGA). Further, a plurality of processing units may be configured by one processor. A first example of the configuration in which a plurality of processing units are configured by one processor is an aspect in which one processor is configured by a combination of one or more CPUs and software and functions as a plurality of processing units. A second example of the configuration is an aspect in which a processor that implements the functions of the entire system including a plurality of processing units using one IC chip is used. A representative example of this aspect is a system-on-chip (SoC). As such, various processing units are configured by using one or more of the various processors as the hardware structure.

In addition, specifically, an electric circuit (circuitry) obtained by combining circuit elements, such as semiconductor elements, is used as the hardware structure of the various processors.

The technology of the present disclosure is not limited to the above-described embodiment and may adopt various configurations without departing from the spirit and scope of the present disclosure. Furthermore, the technology of the present disclosure extends to a computer-readable storage medium that non-temporarily stores the program, in addition to the program.

What is claimed is:

1. A radiographic image detection device comprising:
   a pixel region in which a plurality of pixels detecting radiation are arranged;
   a reading unit that reads a pixel signal from the pixel region; and
   at least one processor,
   wherein the processor performs:
   a first offset image acquisition process of reading the pixel signal from the pixel region in a state in which the radiation is not emitted to acquire at least two first offset images having different accumulation times;
   a second offset image acquisition process of reading the pixel signal from the pixel region in an accumulation time shorter than that of the plurality of first offset images or using binning reading in a state in which the radiation is not emitted to acquire a second offset image;
   a reference image acquisition process of reading the pixel signal from the pixel region using the same reading method as that used for the second offset image and in a state in which gates of the pixels are turned off to acquire a reference image;
   a first dark current distribution image acquisition process of calculating a difference between the two first offset images having different accumulation times to acquire a first dark current distribution image;
   a second dark current distribution image acquisition process of calculating a difference between the second offset image and the reference image to acquire a second dark current distribution image; and
   a determination process of determining whether or not the first offset image and the second offset image need to be reacquired on the basis of a correction error of a corrected image obtained by correcting the first dark current distribution image on the basis of the second dark current distribution image.

2. The radiographic image detection device according to claim 1,
   wherein, in a case in which the correction error is equal to or greater than a threshold value, the processor determines that the first offset image and the second offset image need to be reacquired.

3. The radiographic image detection device according to claim 1,
   wherein the processor acquires the second offset image using the second offset image acquisition process immediately before the first offset image is acquired by the first offset image acquisition process.

4. The radiographic image detection device according to claim 1,
   wherein, in a case in which the pixel signal is read by the binning reading to acquire the second offset image and the reference image, the processor performs the correction after performing an enlargement and reduction process of matching image sizes of the first dark current distribution image and the second dark current distribution image in the determination process.

5. The radiographic image detection device according to claim 1,
   wherein the processor performs:
   a radiographic image generation process of reading the pixel signal from the pixel region in a state in which the radiation is emitted to generate a radiographic image;
   an immediately preceding offset image acquisition process of acquiring an immediately preceding offset image using the same reading method as that used for the second offset image in a state in which the radiation is not emitted immediately before radiography including the radiographic image generation process; and
   a correction process of correcting the radiographic image on the basis of the first offset image, the second offset image, and the immediately preceding offset image.

6. The radiographic image detection device according to claim 5,
   wherein the correction process includes:
   a selection process of selecting the first offset image corresponding to imaging conditions from the at least two first offset images;
   a difference image generation process of generating a difference image between the second offset image and the immediately preceding offset image; and
   a subtraction process of subtracting the first offset image selected by the selection process and the difference image from the radiographic image.

7. A method for operating a radiographic image detection device including a pixel region in which a plurality of pixels detecting radiation are arranged, and a reading unit that reads a pixel signal from the pixel region, the method comprising:
   a first offset image acquisition step of reading the pixel signal from the pixel region in a state in which the radiation is not emitted to acquire at least two first offset images having different accumulation times;

a second offset image acquisition step of reading the pixel signal from the pixel region in an accumulation time shorter than that of the plurality of first offset images or using binning reading in a state in which the radiation is not emitted to acquire a second offset image;

a reference image acquisition step of reading the pixel signal from the pixel region using the same reading method as that used for the second offset image and in a state in which gates of the pixels are turned off to acquire a reference image;

a first dark current distribution image acquisition step of calculating a difference between the two first offset images having different accumulation times to acquire a first dark current distribution image;

a second dark current distribution image acquisition step of calculating a difference between the second offset image and the reference image to acquire a second dark current distribution image; and a determination step of determining whether or not the first offset image and the second offset image need to be reacquired on the basis of a correction error of a corrected image obtained by correcting the first dark current distribution image on the basis of the second dark current distribution image.

8. A non-transitory computer-readable storage medium storing an operation program for operating a radiographic image detection device comprising a pixel region in which a plurality of pixels detecting radiation are arranged, a reading unit that reads a pixel signal from the pixel region, and at least one processor, the operation program causing the processor to perform:

a first offset image acquisition process of reading the pixel signal from the pixel region in a state in which the radiation is not emitted to acquire at least two first offset images having different accumulation times;

a second offset image acquisition process of reading the pixel signal from the pixel region in an accumulation time shorter than that of the plurality of first offset images or using binning reading in a state in which the radiation is not emitted to acquire a second offset image;

a reference image acquisition process of reading the pixel signal from the pixel region using the same reading method as that used for the second offset image and in a state in which gates of the pixels are turned off to acquire a reference image;

a first dark current distribution image acquisition process of calculating a difference between the two first offset images having different accumulation times to acquire a first dark current distribution image;

a second dark current distribution image acquisition process of calculating a difference between the second offset image and the reference image to acquire a second dark current distribution image; and a determination process of determining whether or not the first offset image and the second offset image need to be reacquired on the basis of a correction error of a corrected image obtained by correcting the first dark current distribution image on the basis of the second dark current distribution image.

\* \* \* \* \*